(12) United States Patent
Bose et al.

(10) Patent No.: US 7,931,659 B2
(45) Date of Patent: Apr. 26, 2011

(54) SYSTEM AND METHOD FOR TREATING ISCHEMIC STROKE

(75) Inventors: Arani Bose, New York, NY (US); Vikas Gupta, San Leandro, CA (US); Sean Donahue, Half Moon Bay, CA (US); Delilah Hui, American Canyon, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

(21) Appl. No.: 11/210,636

(22) Filed: Aug. 24, 2005

(65) Prior Publication Data

US 2006/0058838 A1   Mar. 16, 2006

Related U.S. Application Data

(60) Provisional application No. 60/609,028, filed on Sep. 10, 2004, provisional application No. 60/669,779, filed on Apr. 8, 2005, provisional application No. 60/680,605, filed on May 13, 2005.

(51) Int. Cl.
*A61M 29/00* (2006.01)
*A61B 17/22* (2006.01)

(52) U.S. Cl. ........................ 606/127; 606/113

(58) Field of Classification Search .............. 606/200, 606/127, 113–114, 128, 110, 111, 194, 198; 623/1.1, 1.23; 604/107
See application file for complete search history.

(56) References Cited

U.S. PATENT DOCUMENTS

| | | | |
|---|---|---|---|
| 4,046,150 A | 9/1977 | Schwartz et al. | 128/328 |
| 4,611,594 A * | 9/1986 | Grayhack et al. | 606/127 |
| 4,706,671 A | 11/1987 | Weinrib | |
| 4,729,763 A | 3/1988 | Henrie | |
| 4,784,636 A | 11/1988 | Rydell | |
| 4,790,812 A | 12/1988 | Hawkins, Jr. et al. | |
| 4,867,141 A | 9/1989 | Nakada et al. | |
| 4,870,953 A | 10/1989 | DonMicheal et al. | |
| 4,873,978 A | 10/1989 | Ginsburg | |
| 4,898,575 A | 2/1990 | Fischell et al. | |
| 4,927,426 A | 5/1990 | Dretler | |

(Continued)

FOREIGN PATENT DOCUMENTS

DE             27 29 566          1/1979

(Continued)

OTHER PUBLICATIONS

In re PCT Patent Application No. PCT/US2005/030402, "Communication Relating to the Results of the Partial International Search," mailed Dec. 12, 2005, 1 page in length.

*Primary Examiner* — Todd E Manahan
*Assistant Examiner* — Lindsey Bachman
(74) *Attorney, Agent, or Firm* — Kilpatrick Townsend & Stockton LLP

(57) ABSTRACT

A thromboembolic removal system for treating ischemic stroke includes an elongate member and a receiver on a distal portion of the elongate member. The receiver includes structural members arranged to form a sleeve having a central lumen. A plurality of the structural members form engaging elements having apex regions that extend into the central lumen. During use of the thromboembolic removal system, the receiver is advanced over a body of thromboembolic material within a blood vessel, causing the body to be received into the central lumen, and causing the engaging elements to engage the body within the lumen.

23 Claims, 19 Drawing Sheets

U.S. PATENT DOCUMENTS

| | | | |
|---|---|---|---|
| 4,979,939 A | 12/1990 | Shiber | |
| 4,990,134 A | 2/1991 | Auth | |
| 5,011,488 A | 4/1991 | Ginsburg | 606/159 |
| 5,024,651 A | 6/1991 | Shiber | |
| 5,047,040 A | 9/1991 | Simpson et al. | |
| 5,069,664 A | 12/1991 | Guess et al. | |
| 5,100,423 A | 3/1992 | Fearnot | 606/159 |
| 5,100,424 A | 3/1992 | Jang et al. | |
| 5,135,483 A | 8/1992 | Wagner et al. | |
| 5,176,687 A | 1/1993 | Hasson et al. | |
| 5,190,561 A | 3/1993 | Graber | |
| 5,195,954 A | 3/1993 | Schepp-Pesch et al. | |
| 5,248,296 A | 9/1993 | Alliger | |
| 5,273,526 A | 12/1993 | Dance et al. | |
| 5,380,273 A | 1/1995 | Dubrul et al. | |
| 5,417,697 A | 5/1995 | Wilk et al. | |
| 5,423,830 A | 6/1995 | Schneebaum et al. | |
| 5,476,450 A | 12/1995 | Ruggio | |
| 5,501,694 A | 3/1996 | Ressemann et al. | |
| 5,522,819 A | 6/1996 | Graves et al. | |
| 5,549,626 A * | 8/1996 | Miller et al. | 606/200 |
| 5,634,897 A | 6/1997 | Dance et al. | |
| 5,643,297 A | 7/1997 | Nordgren et al. | |
| 5,695,507 A | 12/1997 | Auth | |
| 5,746,758 A | 5/1998 | Nordgren et al. | |
| 5,792,145 A | 8/1998 | Bates et al. | 606/127 |
| 5,827,229 A | 10/1998 | Auth et al. | |
| 5,843,103 A | 12/1998 | Wulfman | |
| 5,911,733 A | 6/1999 | Parodi et al. | |
| 5,938,645 A | 8/1999 | Gordon | |
| 5,972,019 A | 10/1999 | Engelson et al. | |
| 6,001,112 A | 12/1999 | Taylor | |
| 6,066,149 A | 5/2000 | Samson et al. | |
| 6,068,645 A * | 5/2000 | Tu | 606/200 |
| 6,083,259 A | 7/2000 | Frantzen | |
| 6,152,932 A * | 11/2000 | Ternstrom | 606/114 |
| 6,156,048 A | 12/2000 | Wulfman et al. | |
| 6,156,055 A | 12/2000 | Ravenscroft | 606/206 |
| 6,165,199 A | 12/2000 | Barbut | 606/200 |
| 6,203,561 B1 | 3/2001 | Ramee et al. | |
| 6,224,612 B1 | 5/2001 | Bates et al. | |
| 6,306,163 B1 * | 10/2001 | Fitz | 623/1.12 |
| 6,350,266 B1 * | 2/2002 | White et al. | 606/114 |
| 6,350,271 B1 | 2/2002 | Kurz et al. | |
| 6,361,545 B1 * | 3/2002 | Macoviak et al. | 606/200 |
| 6,383,196 B1 | 5/2002 | Leslie et al. | |
| 6,443,966 B1 | 9/2002 | Shiu | |
| 6,458,139 B1 | 10/2002 | Palmer et al. | |
| 6,482,217 B1 | 11/2002 | Pintor et al. | |
| 6,506,166 B1 | 1/2003 | Hendler et al. | |
| 6,511,492 B1 | 1/2003 | Rosenbluth et al. | |
| 6,514,273 B1 | 2/2003 | Voss et al. | |
| 6,517,551 B1 | 2/2003 | Driskill | 606/113 |
| 6,530,923 B1 | 3/2003 | Dubrul et al. | |
| 6,544,276 B1 | 4/2003 | Azizi | |
| 6,551,327 B1 * | 4/2003 | Dhindsa | 606/127 |
| 6,589,263 B1 * | 7/2003 | Hopkins et al. | 606/200 |
| 6,602,204 B2 | 8/2003 | Dubrul et al. | |
| 6,616,676 B2 | 9/2003 | Bashiri et al. | |
| 6,660,014 B2 | 12/2003 | Demarais et al. | |
| 6,666,874 B2 | 12/2003 | Heitzmann et al. | |
| 6,685,722 B1 | 2/2004 | Rosenbluth et al. | |
| 6,692,504 B2 | 2/2004 | Kurz et al. | |
| 6,702,834 B1 | 3/2004 | Boylan et al. | 606/200 |
| 6,719,717 B1 | 4/2004 | Johnson et al. | |
| 6,726,702 B2 | 4/2004 | Khosravi | 606/200 |
| 6,761,727 B1 * | 7/2004 | Ladd | 606/200 |
| 6,808,531 B2 | 10/2004 | Lafontaine et al. | |
| 6,929,634 B2 | 8/2005 | Dorros et al. | 604/523 |
| 6,942,673 B2 | 9/2005 | Bates et al. | |
| 7,063,707 B2 * | 6/2006 | Bose et al. | 606/127 |
| 7,128,718 B2 | 10/2006 | Hojeibane et al. | |
| 7,316,692 B2 | 1/2008 | Huffmaster | |
| 7,686,825 B2 | 3/2010 | Hauser et al. | |
| 2001/0051810 A1 | 12/2001 | Dubrul et al. | 606/159 |
| 2002/0022859 A1 | 2/2002 | Hogendijk | 606/200 |
| 2002/0072764 A1 | 6/2002 | Sepetka et al. | 606/200 |
| 2003/0040762 A1 | 2/2003 | Dorros et al. | 606/159 |
| 2003/0088235 A1 | 5/2003 | Tazi | |
| 2003/0130685 A1 | 7/2003 | Daniel et al. | 606/200 |
| 2003/0150821 A1 * | 8/2003 | Bates et al. | 210/767 |
| 2003/0163158 A1 | 8/2003 | White | 606/200 |
| 2003/0208253 A1 * | 11/2003 | Beyer et al. | 623/1.1 |
| 2003/0212430 A1 | 11/2003 | Bose et al. | 606/200 |
| 2004/0236350 A1 | 11/2004 | Lewis et al. | |
| 2005/0059993 A1 | 3/2005 | Ramzipoor et al. | |
| 2006/0058836 A1 | 3/2006 | Bose et al. | |
| 2006/0058837 A1 | 3/2006 | Bose et al. | |

FOREIGN PATENT DOCUMENTS

WO     WO-01/97697 A1     12/2001

* cited by examiner

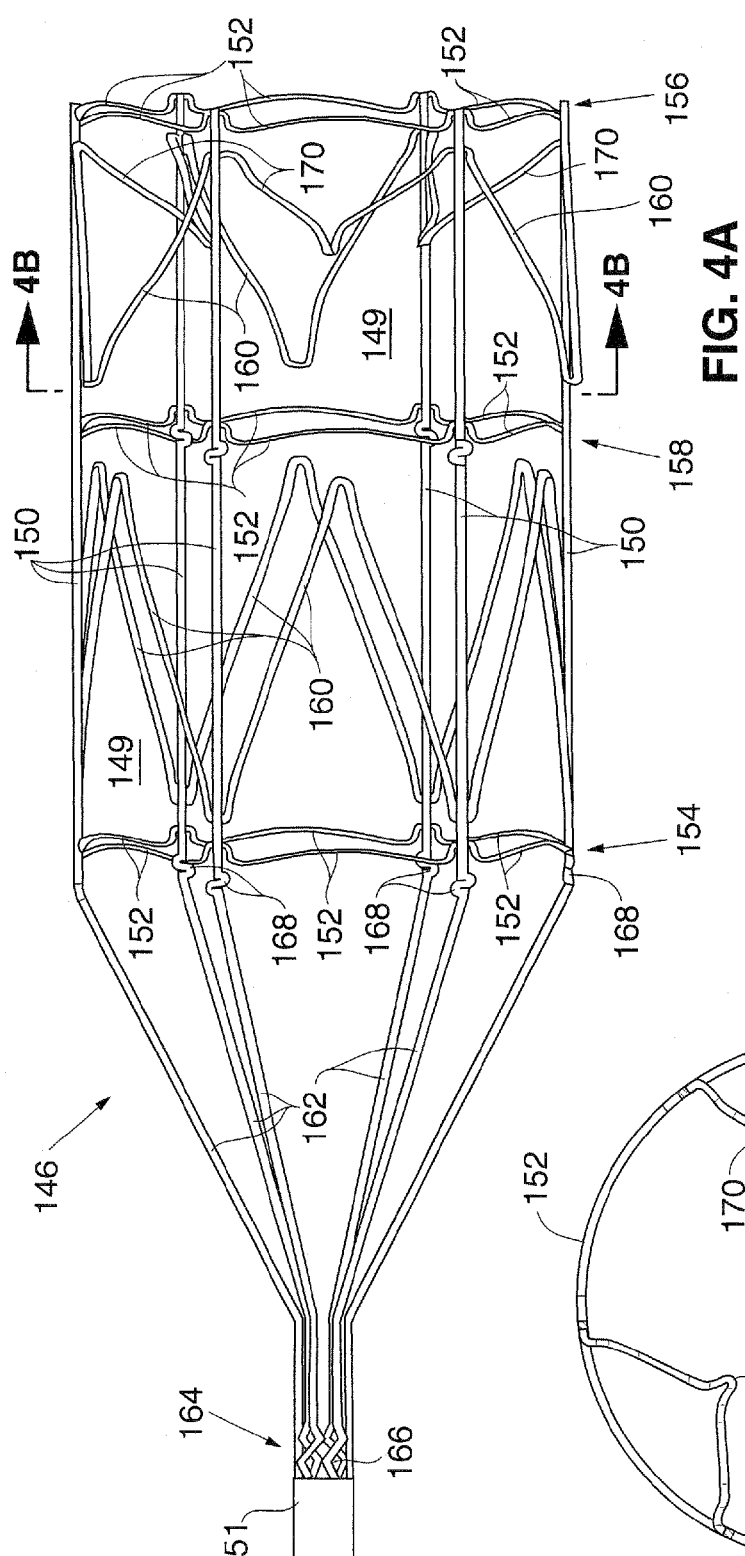
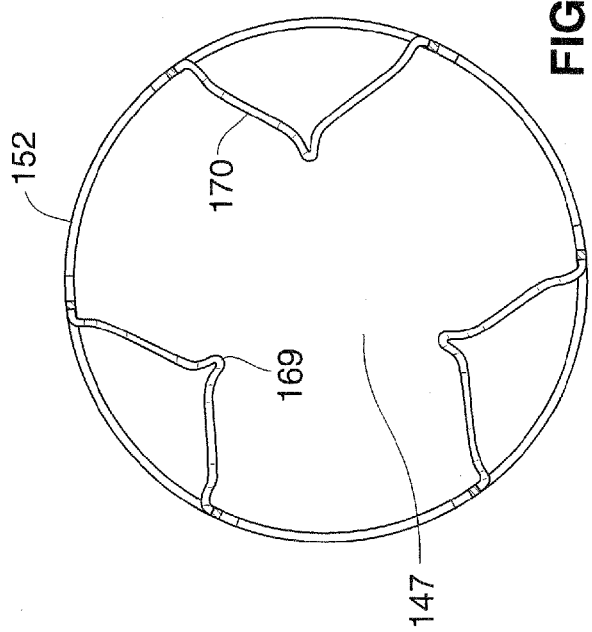
FIG. 4A
FIG. 4B

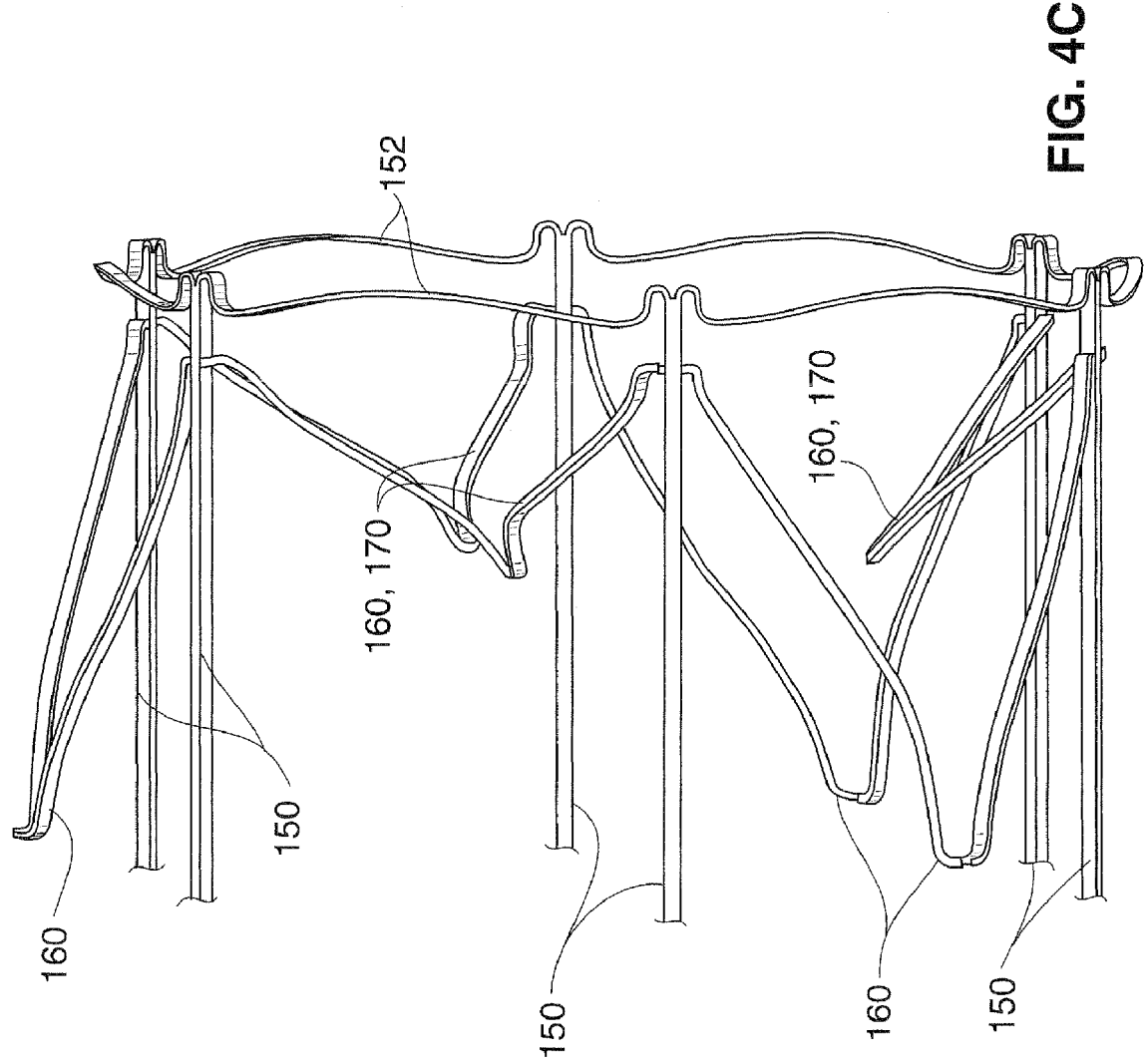

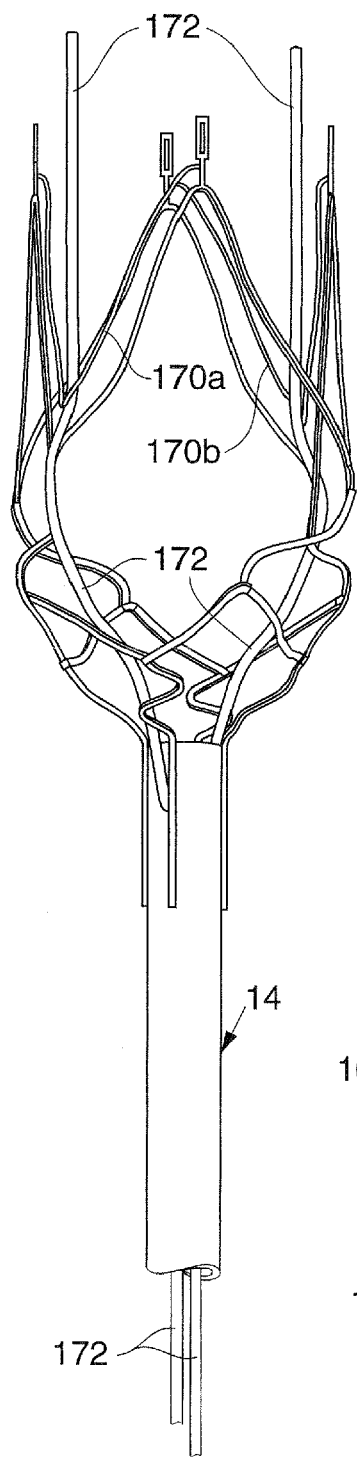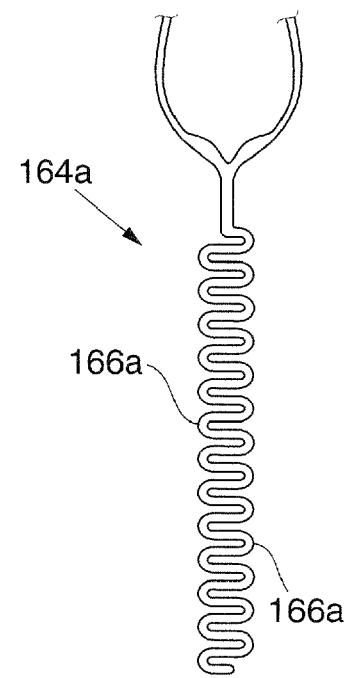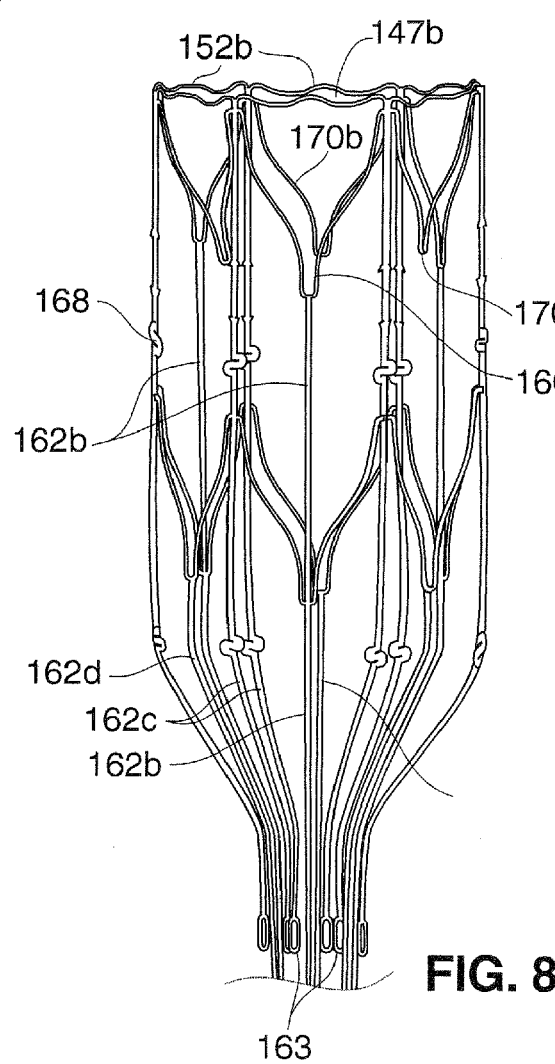
FIG. 6
FIG. 7
FIG. 8A

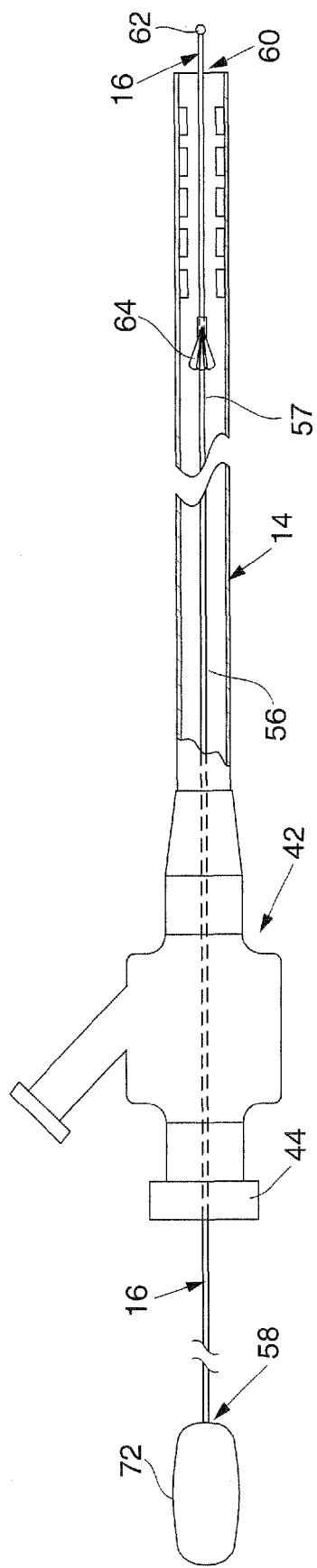
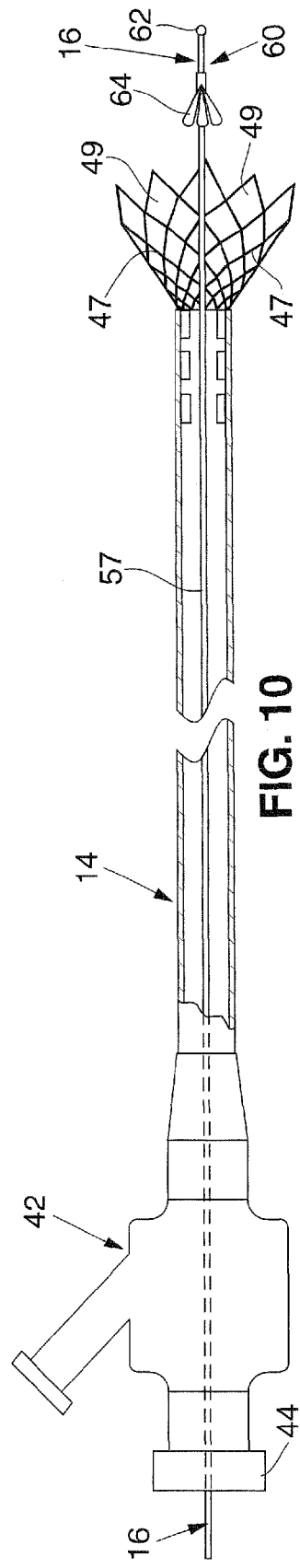

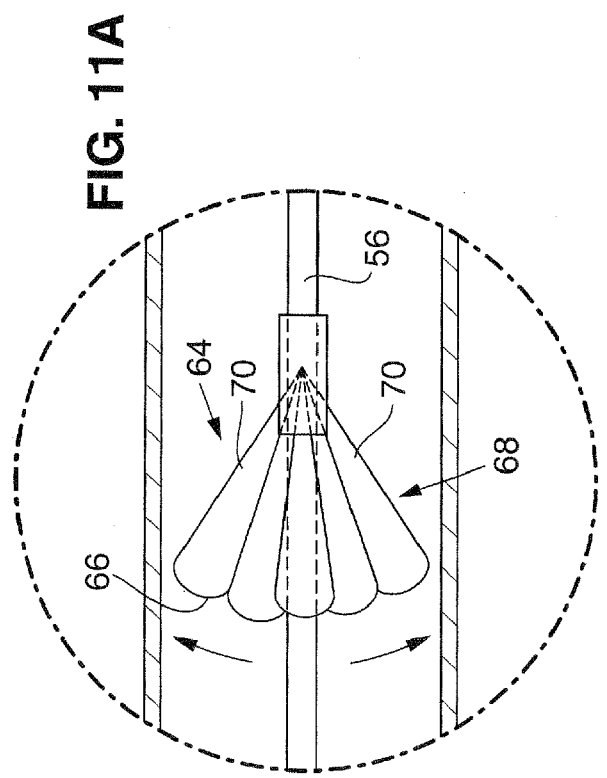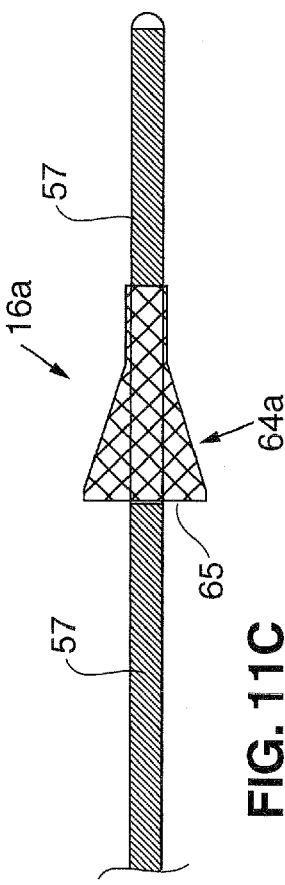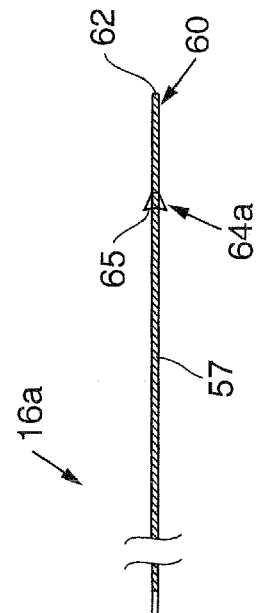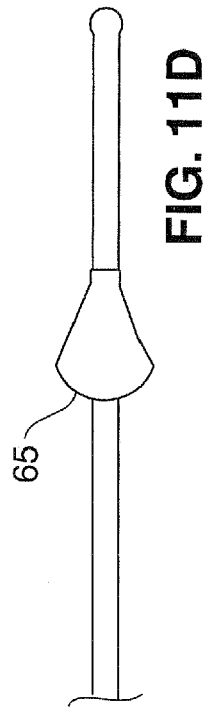

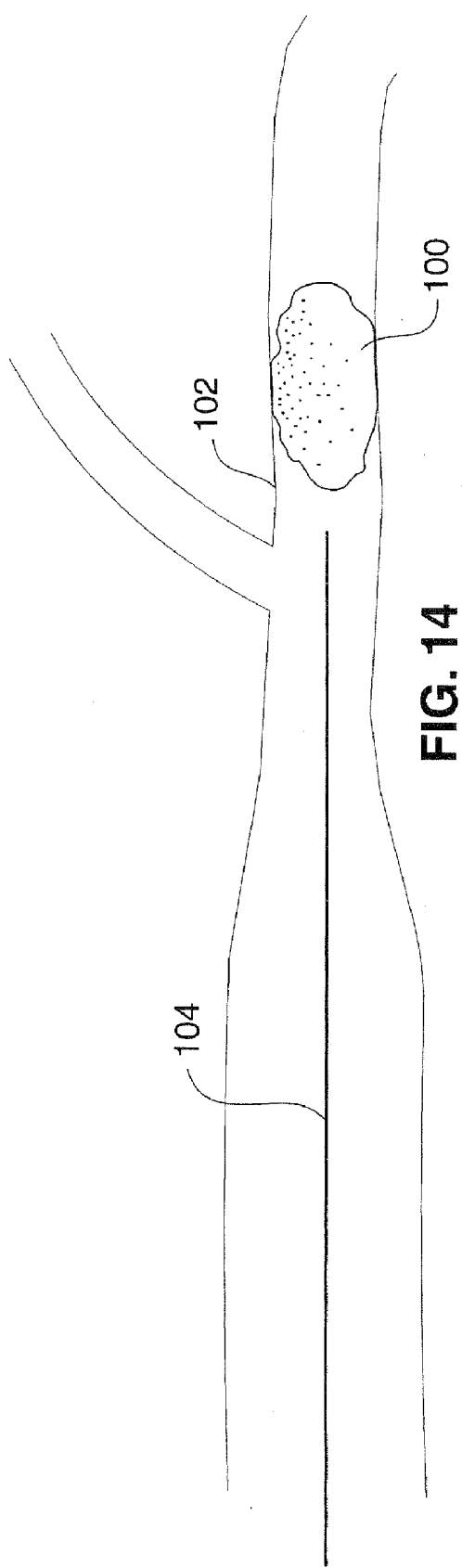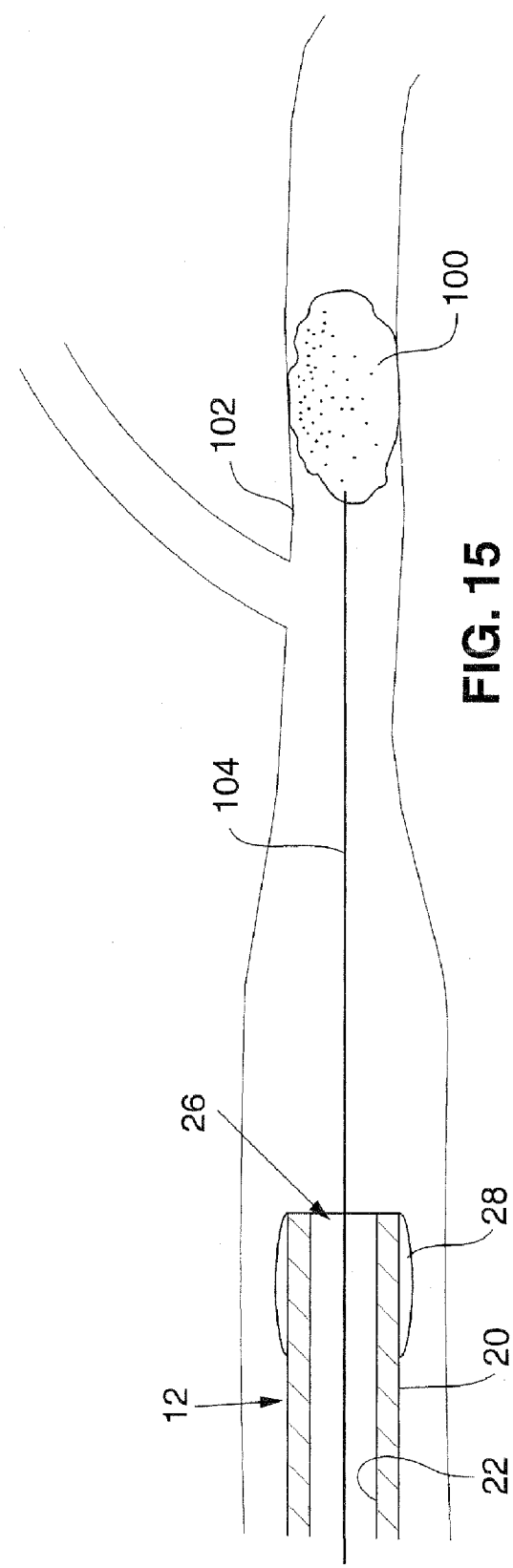

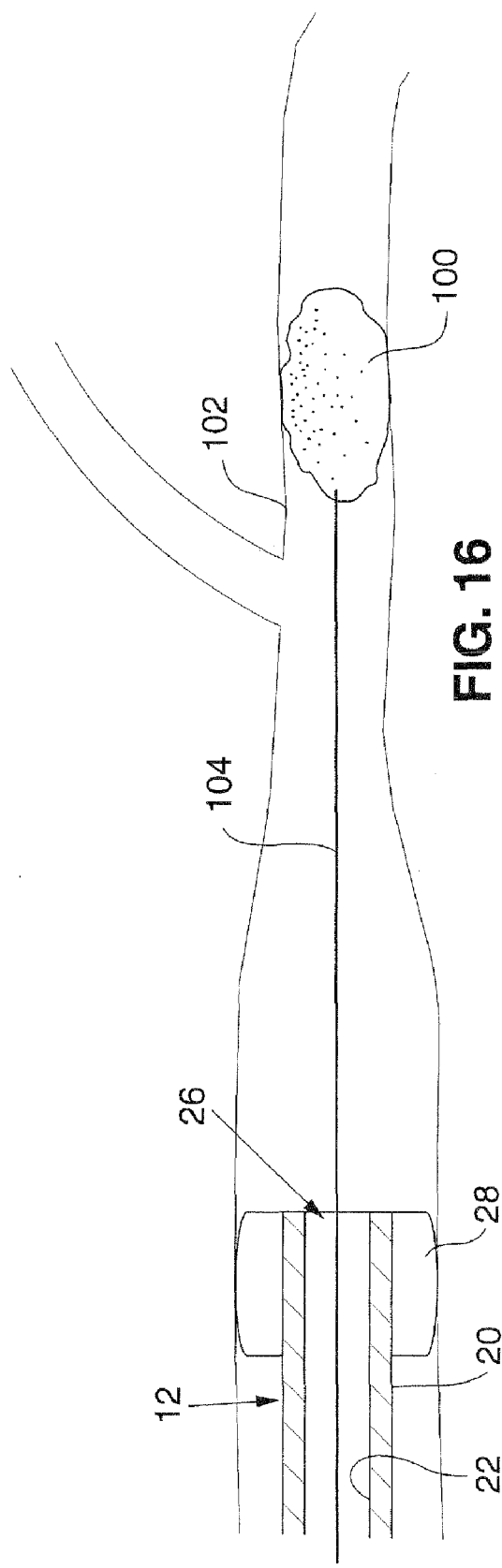
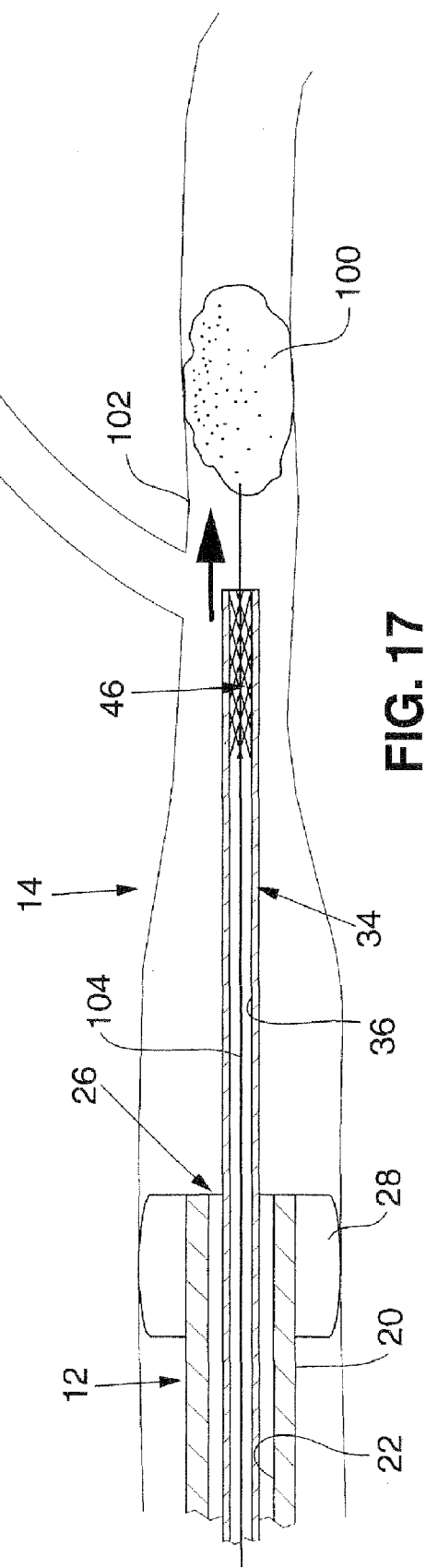

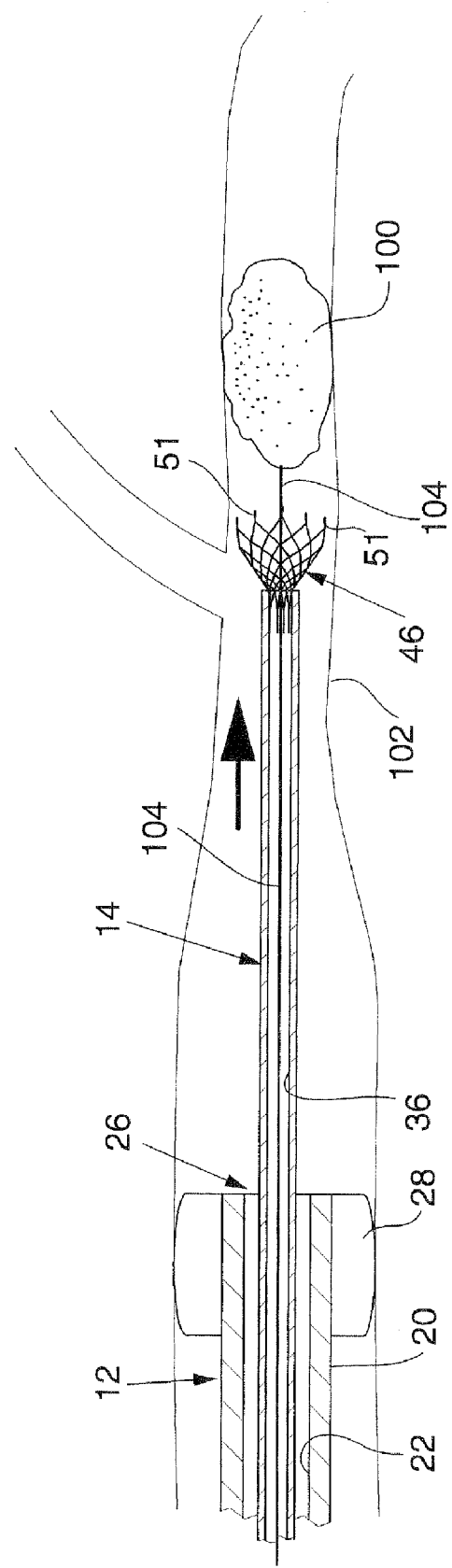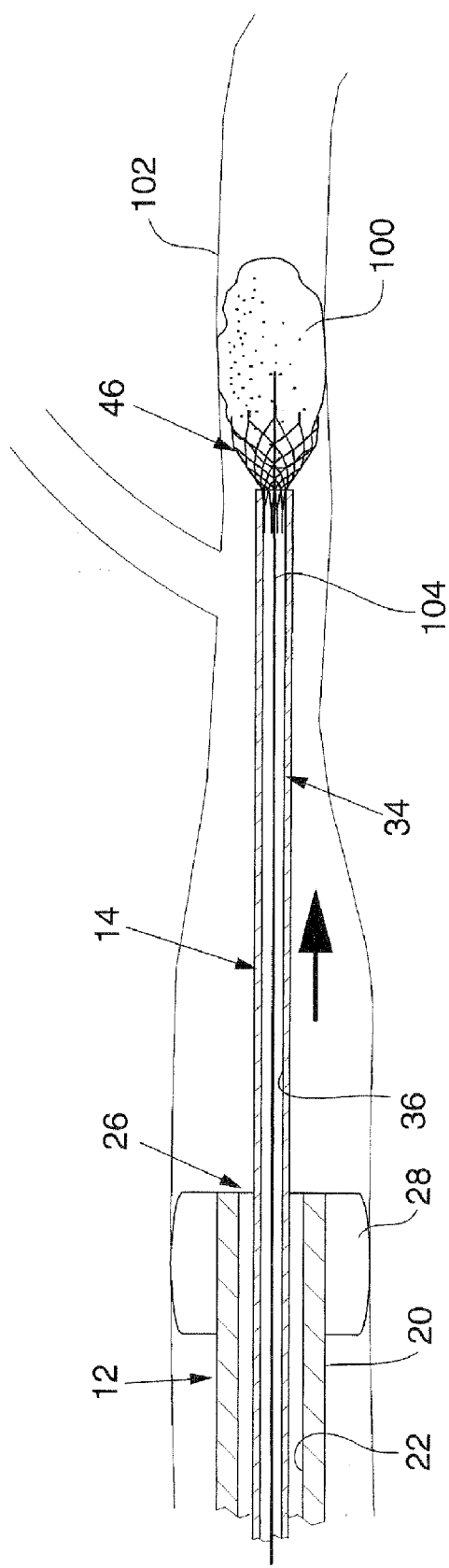

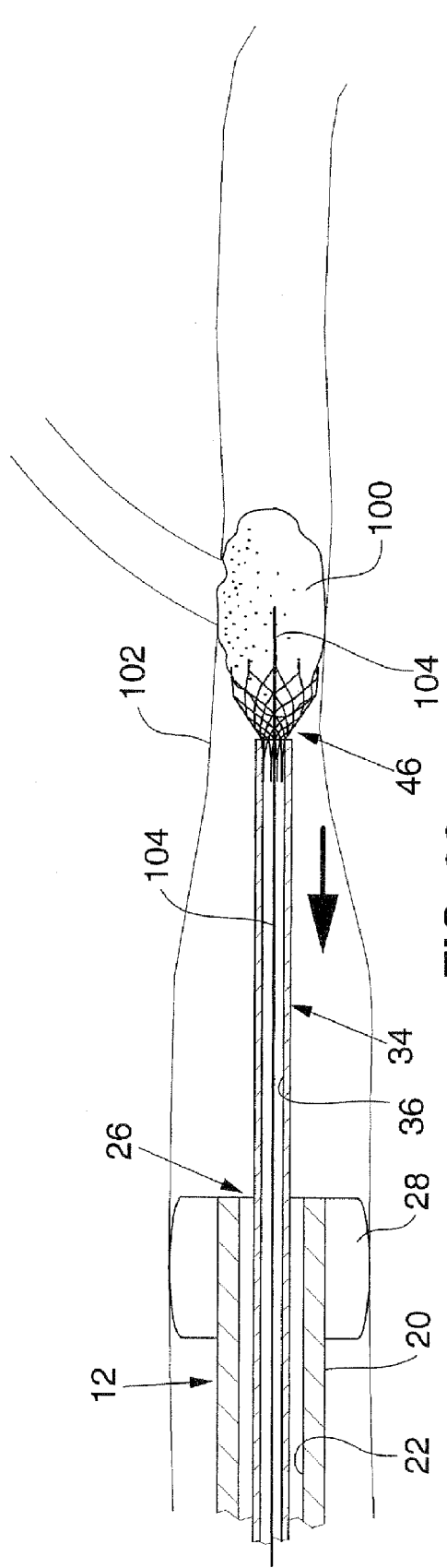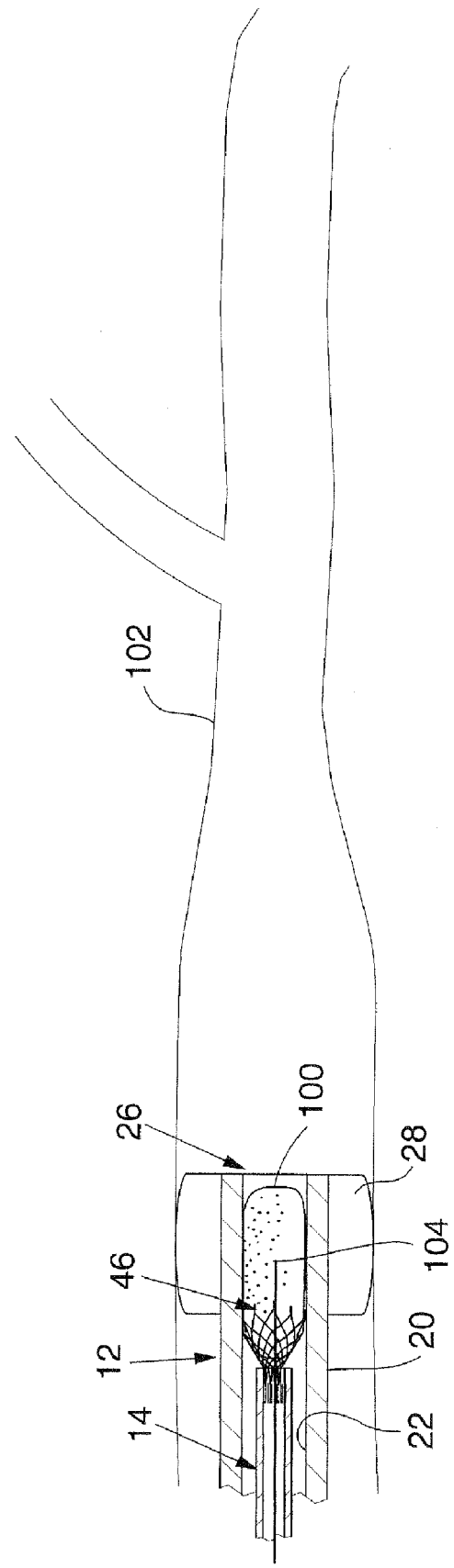

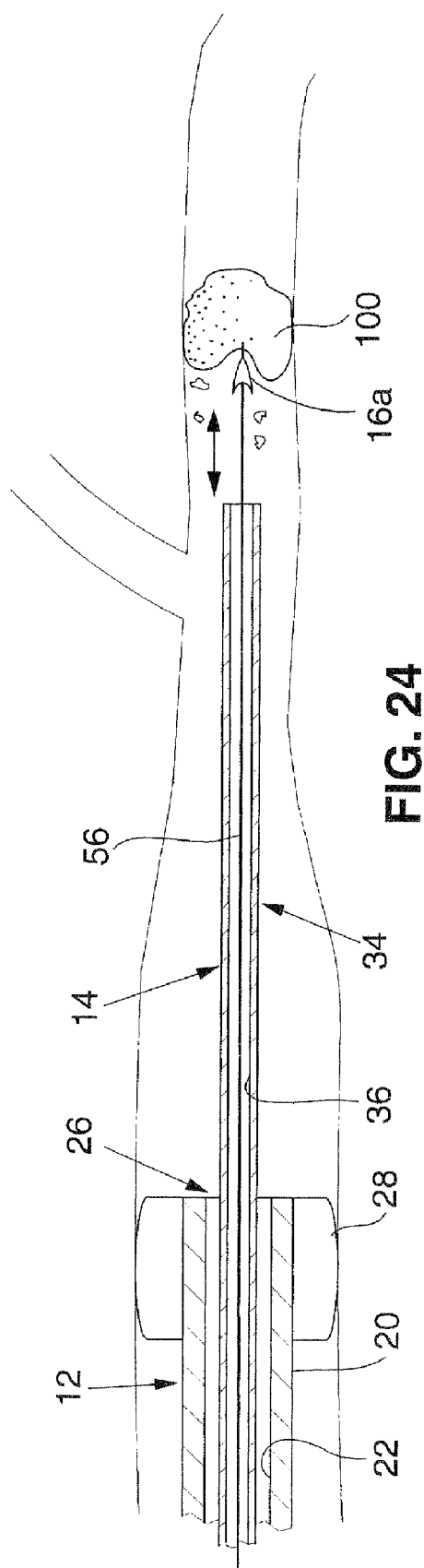
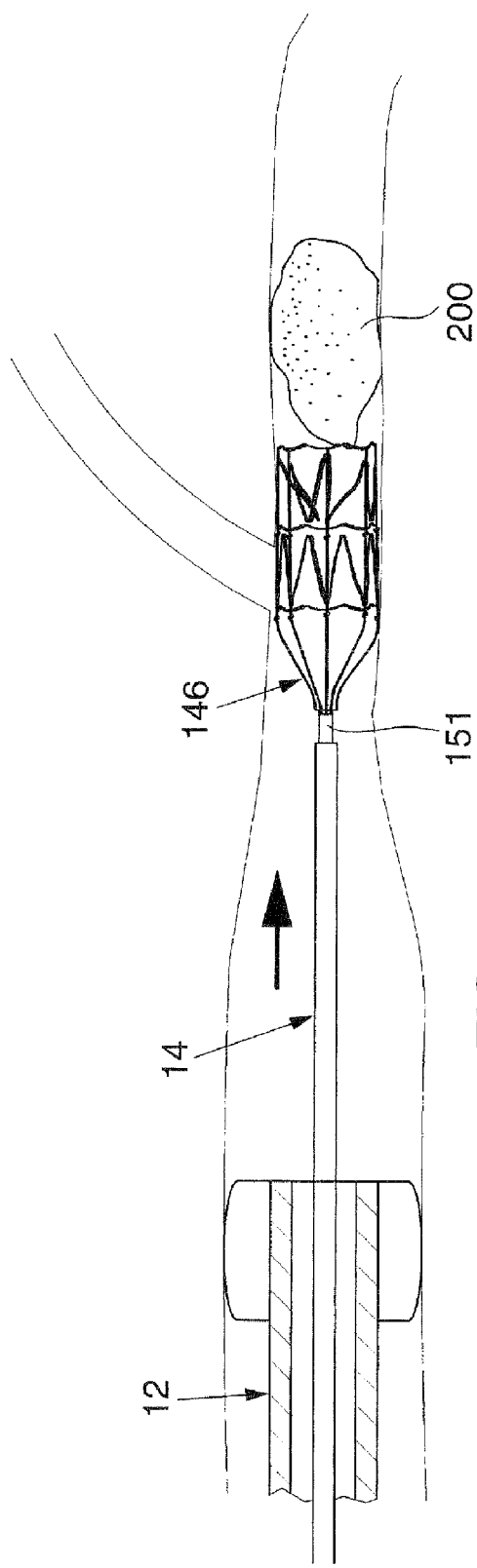

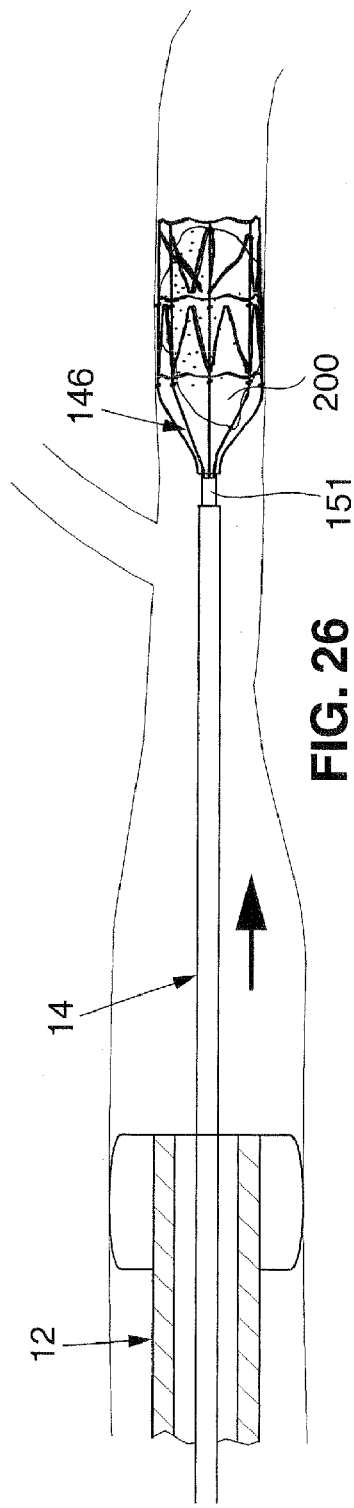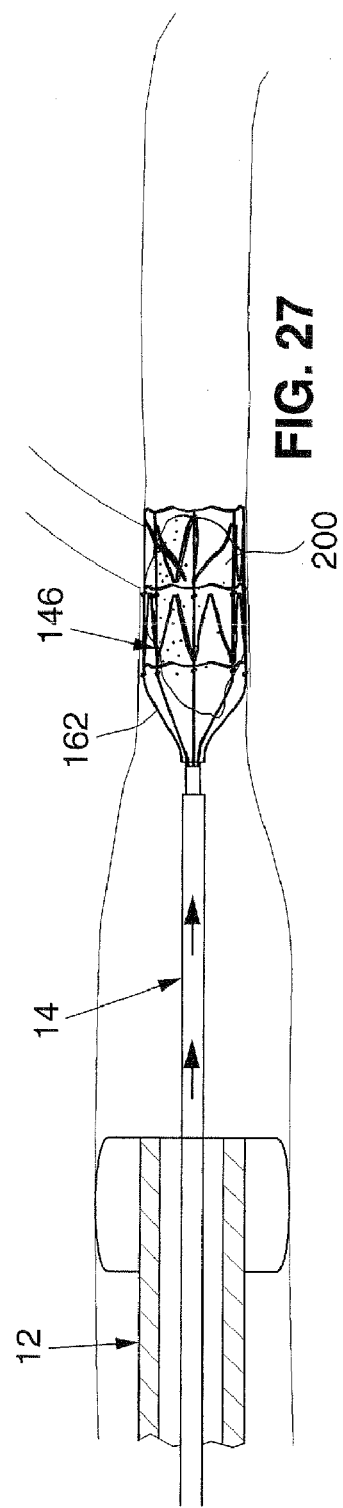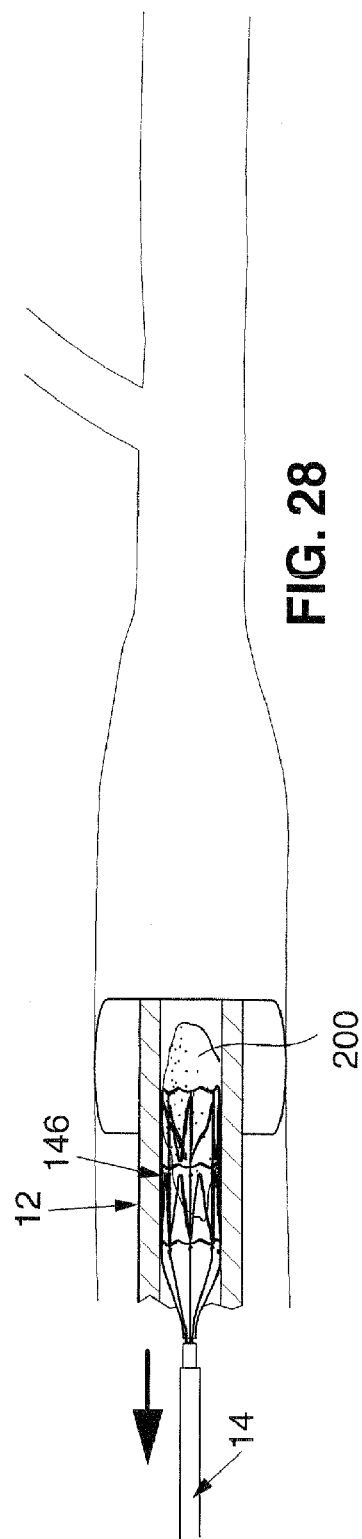

SYSTEM AND METHOD FOR TREATING ISCHEMIC STROKE

This application claims priority to U.S. Provisional Application No. 60/609,028 filed Sep. 10, 2004, U.S. Provisional Application No. 60/669,779, filed Apr. 8, 2005, and U.S. Provisional Application No. 60/680,605, filed May 13, 2005, each of which is fully incorporated herein by reference.

BACKGROUND OF THE INVENTION

I. Field of the Invention

The present invention relates generally to the field of medical treatment and, more particularly, to a system and method for treating ischemic stroke which involves removing a thromboembolism from a cerebral artery of a patient.

II. Discussion of the Prior Art

Stroke is a leading cause of death and disability and a growing problem to global healthcare. In the US alone, over 700,000 people per year suffer a major stroke and, of these, over 150,000 people die. Even more disturbing, this already troubling situation is expected to worsen as the "baby boomer" population reaches advanced age, particularly given the number of people suffering from poor diet, obesity and/or other contributing factors leading to stroke. Of those who survive a stroke, approximately 90% will have long-term impairment of movement, sensation, memory or reasoning, ranging from mild to severe. The total cost to the US healthcare system is estimated to be over $50 billion per year.

Strokes may be caused by a rupture of a cerebral artery ("hemorrhagic stroke") or a blockage in a cerebral artery due to a thromboembolism ("ischemic stroke"). A thromboembolism is a detached blood clot that travels through the bloodstream and lodges so as to obstruct or occlude a blood vessel. Between the two types of strokes, ischemic stroke comprises the larger problem, with over 600,000 people in the US suffering from ischemic stroke per year.

Ischemic stroke treatment may be accomplished via pharmacological elimination of the thromboembolism and/or mechanical elimination of the thromboembolism. Pharmacological elimination may be accomplished via the administration of thombolytics (e.g., streptokinase, urokinase, tissue plasminogen activator (TPA)) and/or anticoagulant drugs (e.g., heparin, warfarin) designed to dissolve and prevent further growth of the thromboembolism. Pharmacologic treatment is non-invasive and generally effective in dissolving the thromboembolism. Notwithstanding these generally favorable aspects, significant drawbacks exist with the use of pharmacologic treatment. One such drawback is the relatively long amount of time required for the thrombolytics and/or anticoagulants to take effect and restore blood flow. Given the time-critical nature of treating ischemic stroke, any added time is potentially devastating. Another significant drawback is the heightened potential of bleeding or hemorrhaging elsewhere in the body due to the thombolytics and/or anticoagulants.

Mechanical elimination of thromboembolic material for the treatment of is chemic stroke has been attempted using a variety of catheter-based transluminal interventional techniques. One such interventional technique involves deploying a coil into a thromboembolism (e.g. via corkscrew action) in an effort to ensnare or envelope the thromboembolism so it can be removed from the patient. Although an improvement over pharmacologic treatments for ischemic stroke, such coil-based retrieval systems have only enjoyed modest success (approximately 55%) in overcoming ischemic stroke due to thromboembolic material slipping past or becoming dislodged by the coil. In the latter case, the dislodgement of thromboembolic material may lead to an additional stroke in the same artery or a connecting artery.

Another interventional technique involves deploying a basket or net structure distally (or downstream) from the thromboembolism in an effort to ensnare or envelope the thromboembolism so it can be removed from the patient. Again, although overcoming the drawbacks of pharmacologic treatment, this nonetheless suffers a significant drawback in that the act of manipulating the basket or net structure distally from the occluded segment without angiographic roadmap visualization of the vasculature increases the danger of damaging the vessel. In addition, removing the basket or net structure may permit if not cause thromboembolic material to enter into connecting arteries. As noted above, this may lead to an additional stroke in the connecting artery.

A still further interventional technique for treating ischemic stroke involves advancing a suction catheter to the thromboembolism with the goal of removing it via aspiration (i.e. negative pressure). Although generally safe, removal via aspiration is only effective with relatively soft thrombus-emboli. To augment the effectiveness of aspiration techniques, a rotating blade has been employed to sever or fragment the thromboembolism, which may thereafter be removed via the suction catheter. While this rotating blade feature improves the effectiveness of such an aspiration technique, it nonetheless increases the danger of damaging the vessel due to the rotating blade.

The foregoing interventional techniques, as well as others in the prior art, all suffer one or more drawbacks and are believed to be sub-optimal for treating ischemic stroke. The present invention is directed at overcoming, or at least improving upon, the disadvantages of the prior art.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 4A is a perspective view depicting an alternate embodiment of a thromboembolic receiver, equipped with a plurality of engagement elements;

FIG. 4B is a cross-section view taken along the plane designated 4B-4B in FIG. 4A;

FIG. 4C is a perspective view illustrating the distal portion of the thromboembolic receiver of FIG. 4A;

FIG. 5 shows it opened and flattened into a sheet so that its features may be more easily viewed;

FIG. 6 is a top view illustrating one embodiment of a flex region for use in flexibly coupling the thromboembolic receiver, such as the receiver of FIG. 4A, to an elongate member or a delivery and aspiration catheter;

FIG. 7 is a perspective view of an alternate thromboembolic receiver, equipped with a plurality of engagement elements capable of being selectively deployed after the deployment of the thromboembolic receiver;

FIG. 8A is perspective view of a thromboembolic receiver having features for facilitating reloading of the receiver into a catheter;

FIGS. 9 and 10 are partial sectional side views of one embodiment of a thromboembolic disrupter or separator in use with a delivery and aspiration catheter;

FIG. 11A is an enlarged view of the separator element forming part of the thromboembolic separator shown in FIGS. 9 and 10;

FIG. 11B is a side elevation view of an alternate embodiment of a thromboembolic separator;

FIG. 11C is an enlarged view of the separator element forming part of the thromboembolic separator shown in FIG. 11B;

FIG. 11D is a side elevation view similar to FIG. 11C showing another alternate embodiment of a thromboembolic separator;

FIG. 14 is a partial section side view illustrating advancement of a guide wire to a thromboembolism;

FIG. 15 is a partial section side view illustrating advancement of the guide and occlusion catheter, with the balloon in a deflated state;

FIG. 16 is a partial section side view illustrating inflation of the balloon occlusion member to arrest the blood flow within the artery containing the thromboembolism;

FIG. 17 is a partial section side view illustrating the step of advancing the delivery and aspiration catheter of FIGS. 1-3 to a point proximal to the thromboembolism according to a method for using the system of FIG. 1;

FIG. 18 is a partial section side view illustrating deployment of the thromboembolic receiver of FIGS. 1-3;

FIG. 19 is a partial section side view illustrating advancement of the delivery and aspiration catheter of FIGS. 1-3 distally such that the thromboembolic receiver of FIGS. 1-3 engages (fully or partially) the thromboembolism;

FIGS. 20 and 21 are partial section side views illustrating movement of the thromboembolic receiver of FIGS. 1-3 into the guide and occlusion catheter so as to remove the thromboembolism;

FIG. 24 is a partial section view illustrating independent use of the thromboembolic separator of FIGS. 1 and 9-11C to fragmentize and/or soften the thromboembolism and/or aid aspiration;

FIGS. 25 and 26 are partial section side views illustrating advancement of the thromboembolic receiver of FIGS. 4-6 distally such that it envelopes the thromboembolism; and FIGS. 27 and 28 are a partial section side views illustrating withdrawal of the thromboembolic receiver of FIGS. 4-6 and the delivery and aspiration catheter into the guide and occlusion catheter so as to remove the thromboembolism.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The thromboembolic removal system disclosed herein boasts a variety of inventive features and components that warrant patent protection, both individually and in combination.

System Features

Figure 1:
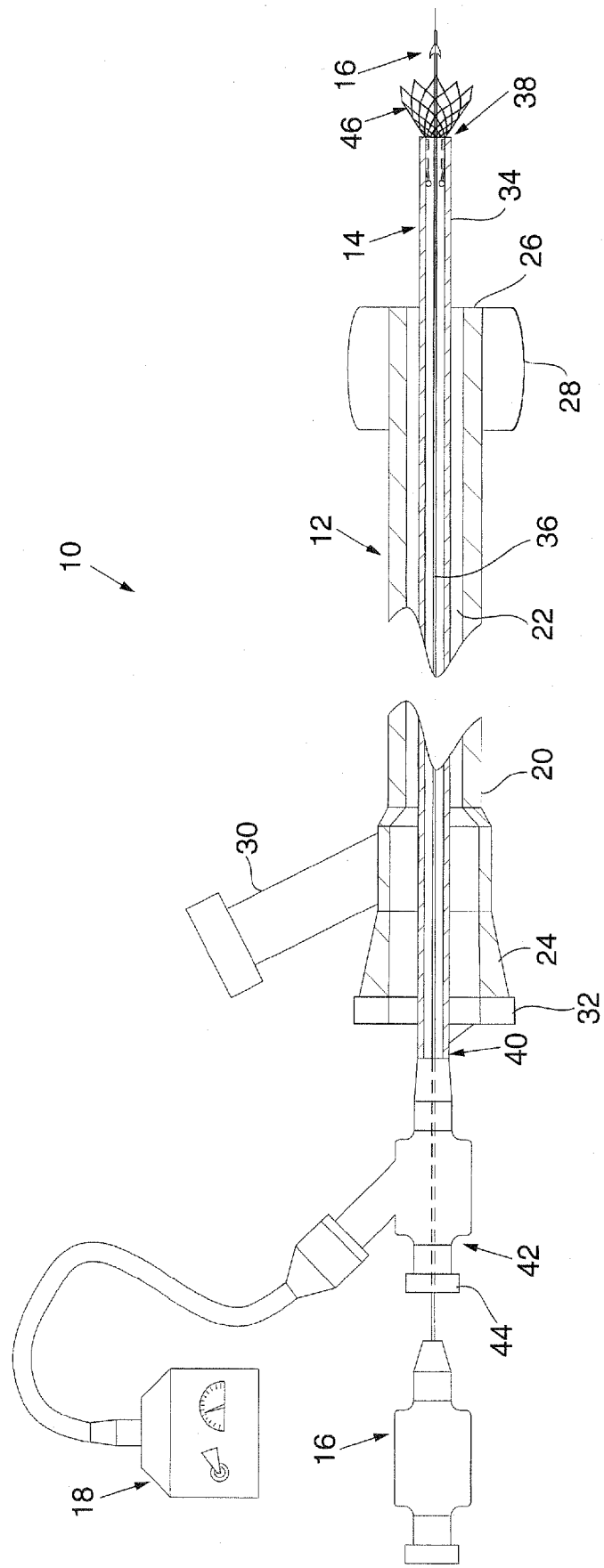
FIG. 1 is a partial sectional side view of one embodiment of a thromboembolic removal system, including a guide and occlusion catheter, a delivery and aspiration catheter, an aspiration pump, a thromboembolic receiver, and a thromboembolic separator.

FIG. 1 illustrates an exemplary embodiment of a thromboembolic removal system 10. The thromboembolic removal system 10 includes a guide and occlusion catheter 12, a delivery and aspiration catheter 14, a thromboembolic disrupter or separator 16, and an aspiration pump 18. As will be described in greater detail below, the thromboembolic removal system 10 advantageously provides the ability to remove a thromboembolism from a cerebral artery within a patient while overcoming the drawbacks and limitations of the prior art.

The guide and occlusion catheter 12 includes a tubular catheter member 20 having a main lumen 22 extending between a proximal end 24 and a distal end 26. The catheter member 20 may be constructed from any number of compositions having suitable biocompatibility and strength characteristics, and may be dimensioned in any number of suitable sizes and lengths depending upon the entry point into the vasculature, the location of the thromboembolism, variances in patient anatomy, and any extenuating circumstances. In an exemplary embodiment, the catheter member 20 may be constructed from nylon with embedded stainless steel braid and dimensioned having a length ranging from 70 cm to 110 cm and a diameter ranging from 5 French (0.065 inch) to 9 French (0.117 inch). A balloon occlusion member 28 is disposed at or near the distal end 26. To selectively inflate the occlusion member 28, an inflation port 30 is provided in fluid communication with the occlusion member 28 via at least one lumen (not shown) disposed within the wall of the tubular catheter member 20. A seal 32 is provided for passing the delivery and aspiration catheter 14 through the main lumen 22 of the guide and occlusion catheter 12 in leak-free, hemostatic fashion.

The delivery and aspiration catheter 14 includes a tubular catheter element 34 having a main lumen 36 extending between a distal end 38 and a proximal end 40. The catheter member 34 may be constructed from any number of compositions having suitable biocompatibility and strength characteristics, and may be dimensioned in any number of suitable sizes and lengths depending upon the entry point into the vasculature, the location of the thromboembolism, variances in patient anatomy, and any extenuating circumstances. In an exemplary embodiment, the catheter member 34 may be constructed from pebax with embedded stainless steel braid and dimensioned having a length ranging from 130 cm to 170 cm and a diameter ranging from 2.5 French (0.032 inch) to 5 French (0.065 inch).

The delivery and aspiration catheter 14 also includes a hub assembly 42 coupled to the proximal end 40 for the purpose of coupling the lumen 36 to the aspiration pump 18. The hub assembly 42 also includes a seal 44 for allowing the passage of the thromboembolic separator 16 (as well as any pushing devices to deploy a receiver element 46, as will be discussed below) through the lumen 36 in leak-free, hemostatic fashion. The lumen is preferably coated with PTFE or another of the various suitable lubricious materials known in the art.

Figure 2:
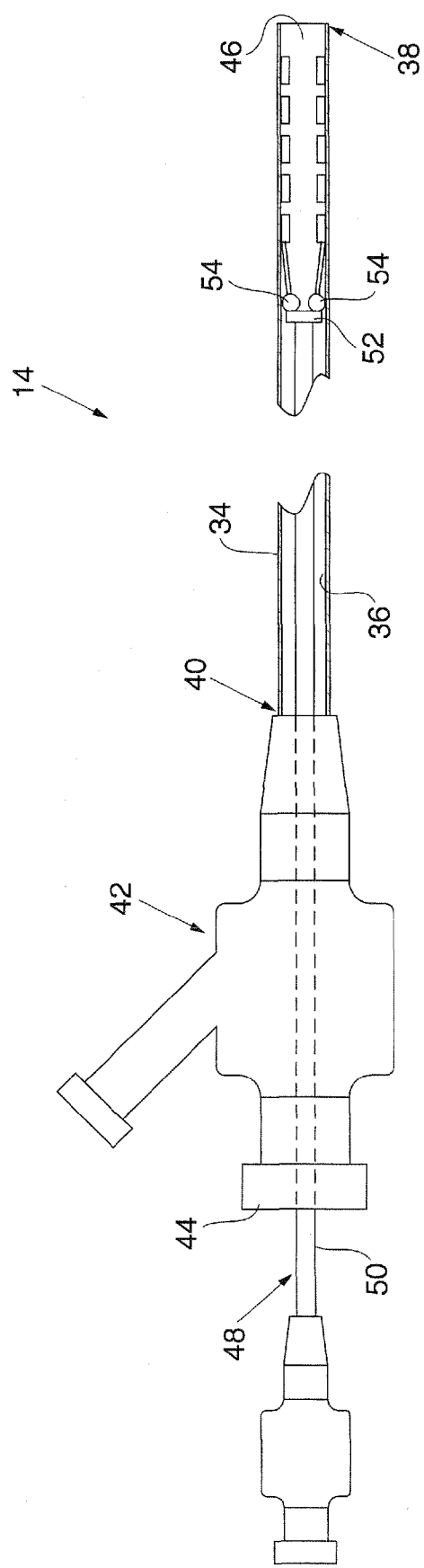
FIG. 2 is a partial sectional side view of a delivery and aspiration catheter forming part of the thromboembolic removal system shown in FIG. 1, illustrating a thromboembolic receiver element in an undeployed state.
Figure 3:
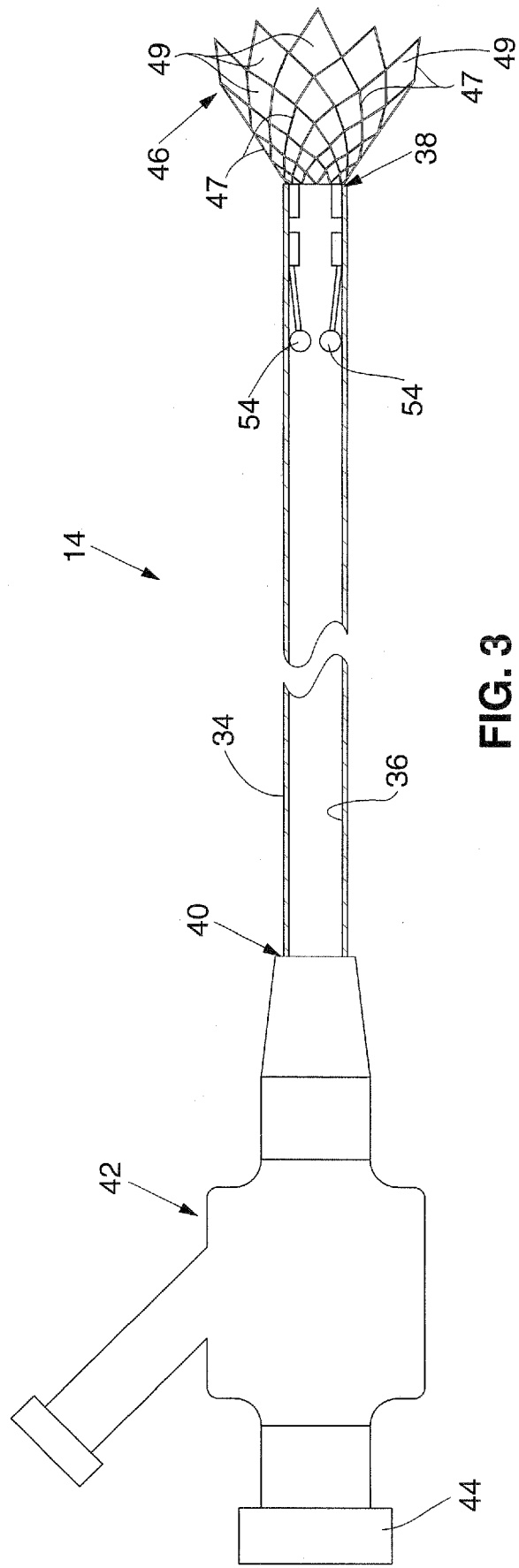
FIG. 3 is a partial sectional side view of a delivery and aspiration catheter forming part of the thromboembolic removal system shown in FIG. 1, illustrating the thromboembolic receiver element in a deployed state.

As best viewed with reference to FIGS. 2-3, the thromboembolic receiver element 46 is capable of being retained in a withdrawn or undeployed state within the lumen 36 (FIG. 2) and selectively pushed out and/or unsheathed from the distal end 38 into a deployed state (FIG. 3). The thromboembolic receiver 46 may be constructed from any number of compositions having suitable biocompatibility and strength characteristics, and may be dimensioned in any number of suitable sizes and lengths depending upon the location of the thromboembolism, variances in patient anatomy, and the size and shape of the thromboembolism. As best viewed in FIGS. 3 and 5, the thromboembolic receiver 46 is formed from a plurality of strut members 47, which upon being deployed, create a multitude of generally diamond-shaped openings 49 along the periphery of the thromboembolic receiver 46. According to one embodiment, as shown in FIGS. 18-23, the resulting points at the distal region of the thromboembolic receiver 46 are equipped with blunt tip features 51 to facilitate passage of the thromboembolic receiver 46 through the cerebral artery without snagging or becoming otherwise stuck on the arterial walls or branch vessels leading into the cerebral artery.

A pusher element 48 may be provided within the catheter element 34 for use in advancing or pushing the receiver element 46 from within the lumen 36 to assume a fully or partially deployed state. By way of example only, the pusher element 48 comprises an elongate member 50 of suitable construction (e.g. wire or wire-wound) having a distal abutment 52 dimensioned to contact proximal terminal(s) 54 forming part of (or coupled to) the receiver element 46. Although not shown, it will be appreciated that the pusher element 48 may comprise any number of suitable devices for pushing the receiver element 46 for deployment, including but not limited to a catheter having a distal end dimensioned to contact the proximal terminal(s) 54 of the receiver element 46. In one embodiment, such a pusher-catheter may have an internally disposed lumen dimensioned to receive and/or pass the thromboembolic separator 16.

FIG. 4A illustrates a thromboembolic receiver 146 of an alternate embodiment. The thromboembolic receiver 146 may be constructed from any number of compositions having suitable biocompatibility and strength characteristics, and may be dimensioned in any number of suitable sizes and lengths depending upon the location of the thromboembolism, variances in patient anatomy, and the size and shape of the thromboembolism. In a preferred embodiment, the thromboembolic receiver 146 is constructed from Nitinol with "shape memory" or superelastic characteristics. In this fashion, the thromboembolic receiver 146 is capable of being retained in a constrained form or shape prior to deployment. The receiver may be formed by laser cutting features into a length of Nitinol tubing, and then chemically etching and shape-setting the material one or more times using methods known to those skilled in the art.

Referring to FIG. 4A, receiver 146 is mounted to an elongate member 151 preferably proportioned to extend through lumen 36 (FIG. 1) of the delivery and aspiration catheter 14. Strut members or "legs" 162 extend between receiver 146 and elongate member 151 and are preferably attached to the elongate member 151 using bonding, shrink tubing, or other known methods. In a preferred embodiment, member 151 is an elongate rod, catheter, wire or other elongate member. In this embodiment, the thromboembolic receiver 146 is proportioned so that it may be constrained in a compressed position within the delivery and aspiration catheter 14 (in a manner similar to that shown in FIGS. 1-3). Alternatively, the elongate member 151 may be the delivery and aspiration catheter 14, in which case the receiver 146 and delivery and aspiration catheter 14 are proportioned to extend through the guide and occlusion catheter 12.

In either event, the thromboembolic receiver 146 may be automatically deployed—due to the shape memory or superelastic characteristics of Nitinol—by simply advancing the thromboembolic receiver 146 out of the element constraining it in the undeployed state (e.g. the guide and occlusion catheter 12 or the delivery and aspiration catheter 14). Once deployed, the thromboembolic receiver 146 may be employed to retrieve a thromboembolism. The dimensions of the receiver 146 are preferably selected such that when it is in an expanded condition at body temperature, the exterior surface of the distal portion of the receiver contacts the surrounding walls of the blood vessel. In one embodiment suitable for most intracranial vessels, the receiver may expand to a maximum outer diameter of approximately 2-6 mm, and more preferably 2-5 mm. For other applications such as procedures within the common carotid artery, a maximum outer diameter in the range of approximately 6-9 mm may be suitable.

The thromboembolic receiver 146 may be formed having any of a variety of suitable geometries and features without departing from the scope of the present invention. According to one embodiment shown in FIGS. 4A and 5, the thromboembolic receiver 146 is formed from a plurality of strut members, which upon being deployed, create a multitude of generally rectangular openings 149 (best viewed in FIG. 5) along the periphery of the thromboembolic receiver 146. This is accomplished, by way of example, by providing a plurality of longitudinal strut members or "standards" 150 (which are generally parallel to the longitudinal axis of the delivery and aspiration catheter 14), and a plurality of transverse strut members 152 (which extend generally perpendicularly between the adjacent standards). In a preferred embodiment, the strut members collectively define a generally cylindrical distal portion having a central lumen 147 as shown in FIG. 4B.

Figure 5:
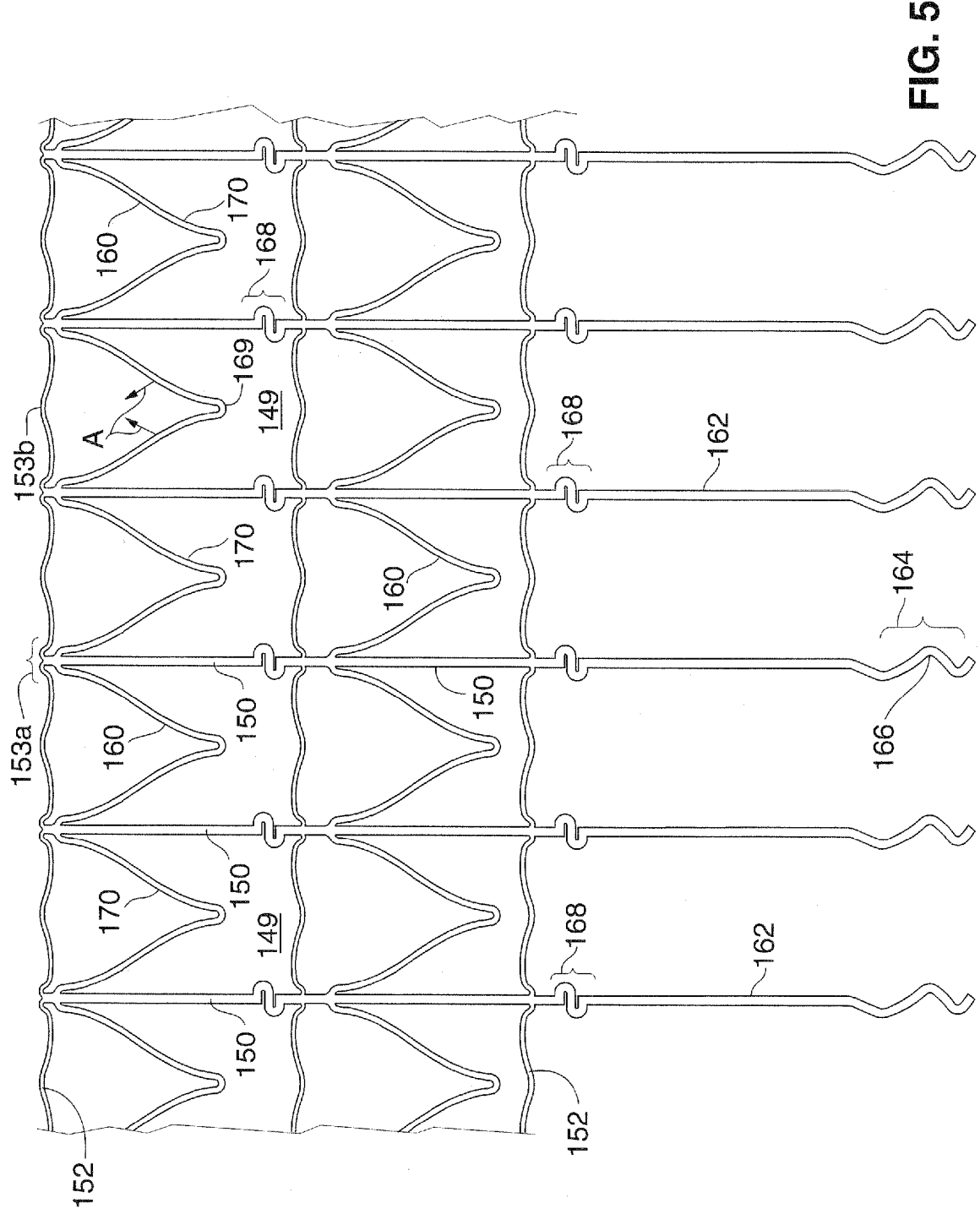
FIG. 5 is a plan view of the alternate thromboembolic receiver of FIG. 4. Although the receiver is preferably a tubular structure.

The transverse strut members 152 may include any number of curves or undulations, such as curves 153*a* shown near the points of intersection between the transverse strut members 152 and the standards 150, as well as the curves 153*b* midway between the points of intersection as shown in FIG. 5. Such curves or undulations help allow the thromboembolic receiver 146 to fold into a compressed or constrained state, which is required in order to dispose the thromboembolic receiver 146 within the delivery and aspiration catheter 14 or within the guide and occlusion catheter 12.

The transverse strut members 152 form, in a preferred embodiment, a proximal cuff 154 located closest to the delivery and aspiration catheter 14, a distal cuff 156 located at the distal or open end of the thromboembolic receiver 146, and a middle cuff 158 located at some point between the proximal and distal cuffs. Each cuff (proximal 154, middle 158, and distal 156) is a circumferential ring designed to enhance the structural support and stability of the thromboembolic receiver 146, as well as to aid in maintaining the thromboembolic receiver 146 in a desired shape upon deployment (for improved apposition to the vessel wall to optimize thromboembolic retrieval).

The structural support provided by the cuffs 154-158 may be augmented by providing one or more stabilizing strut members 160 within one or more of the generally rectangular openings 149. According to one embodiment, these stabilizing strut members 160 may take the form of a "V" extending from either the proximal end or distal end of a given generally rectangular opening 149 within the thromboembolic receiver 146. In a preferred embodiment, such "V" shaped stabilizing strut members 160 are provided within the proximal and distal set of generally rectangular openings 149 within the thromboembolic receiver 146. This advantageously adds to the structural stability of the proximal and distal regions of the thromboembolic receiver 146. Regardless of their specific shape, the stabilizing strut members 160 preferably include folding regions or apexes 169 that allow them to fold at the apexes 169 (see arrows A in FIG. 5) when the receiver is compressed into the collapsed position. Additionally, the receiver is preferably constructed so as to permit the strut members 160 to fold in the region where they intersect with other elements forming the receiver (e.g. in the FIG. 5 embodiment, the region of intersection between strut members 160 and standards 150).

While structural stability of the thromboembolic receiver 146 is a desired goal, it is also desired to have certain aspects of flexibility. According to one embodiment, relative flexibility is provided at the junction between the thromboembolic receiver 146 and the elongate member 151 (or the distal end of the delivery and aspiration catheter 14). This is accomplished, by way of example only, by providing the plurality of connector strut members or "legs" 162 extending between the proximal cuff and the elongate member 151 to include (as best viewed in FIG. 5) a flex region 164 near the distal end of the elongate member 151. The flex regions 164 may be formed into any shape that will add flexibility to the strut members 162 without comprising the user's ability to transmit axial forces along the length of the strut members 162. In an alternate embodiment shown in FIG. 6, the flex regions 164a may comprise a plurality of meandering "S" shaped struts 166a at the proximal ends of the connector struts 162. According to another embodiment, a flex region or spring region 168 (FIG. 5) (which may comprise one or more "S" shaped curves or other shapes designed to provide flexibility while maintaining adequate column strength) may be provided at the junction between adjacent longitudinal strut members or standards 150. In both instances, such flex regions 164, 168 are advantageous in that they allow the thromboembolic receiver 146 to better track and follow tortuous vessels without sacrificing needed column strength.

According to a further embodiment, the thromboembolic receiver 146 may also include a variety of features to augment engagement between the thromboembolic receiver 146 and the thromboembolism. This may be accomplished, by way of example only, by providing a plurality of engagement elements 170 on the thromboembolic receiver. As best viewed in FIGS. 4A, 4B and 5, the engagement elements 170 may, according to one embodiment, take the form of a "V" shaped structure coupled at or near the distal end of the thromboembolic receiver 146 and extending between adjacent standards 150. The engagement elements preferably angle into the lumen 147 of the thromboembolic receiver (see FIGS. 4B and 4C) so as to permit engagement of a thromboembolism captured within the lumen. Any number of engagement elements 170 may be employed without departing from the scope of the present invention. In one embodiment, three (3) separate engagement elements 170 may be employed, each being disposed one hundred and twenty (120) degrees from one another along the periphery of the thromboembolic receiver 146. In a preferred embodiment, the engagement elements 170 take the form of a plurality of the stabilizing strut members 160 as shown in FIGS. 4A and 5.

The engagement elements 170 may be deployed automatically when the thromboembolic receiver 146 is deployed (as shown in FIG. 4-5). In accordance with another aspect of the invention shown in FIG. 7, the engagement elements 170a may also be selectively deployed at any point following the deployment of the thromboembolic receiver 146a. According to the FIG. 7 embodiment, the selective deployment of the engagement elements 170a is accomplished by passing one or more elongate elements 172 through the thromboembolic receiver 146a such that the engagement elements 170a are prevented from extending medially into the lumen of the thromboembolic receiver 146. When deployment is desired, a user need only pull the elongate elements 172 in a proximal direction (towards the user) until the engagement elements 170a are set free from the constraint of the elongate elements 172. When this occurs, the "shape memory" or superelastic nature of the engagement elements 170a will cause them to assume their natural state, extending medially into the lumen of the thromboembolic receiver 146a. In this fashion, the engagement elements 170a will engage the thromboembolism and thus aid or enhance the ability of the thromboembolic receiver 146a to remove a thromboembolism.

The thromboembolic receiver may be provided with features that allow a surgeon to retract the receiver back into the delivery and aspiration catheter after the receiver has been partially or fully deployed into a blood vessel. This might be necessary if, perhaps, the surgeon receives angiographic or tactile feedback indicating that a separator would be a preferred tool for removal of a particular embolism, or that a receiver of a different size would be more suitable for a particular procedure.

FIG. 8A illustrates one example of an embodiment of a thromboembolic receiver 146b that is similar to the receiver 146 of FIG. 4, but that includes features that facilitate reloading of the receiver into the delivery and aspiration catheter 14. As shown, receiver 146b of the FIG. 8A embodiment includes a single, distal, cuff 152b and a plurality of longitudinal strut members 150b extending proximally from the cuff 152b.

Figure 8B:
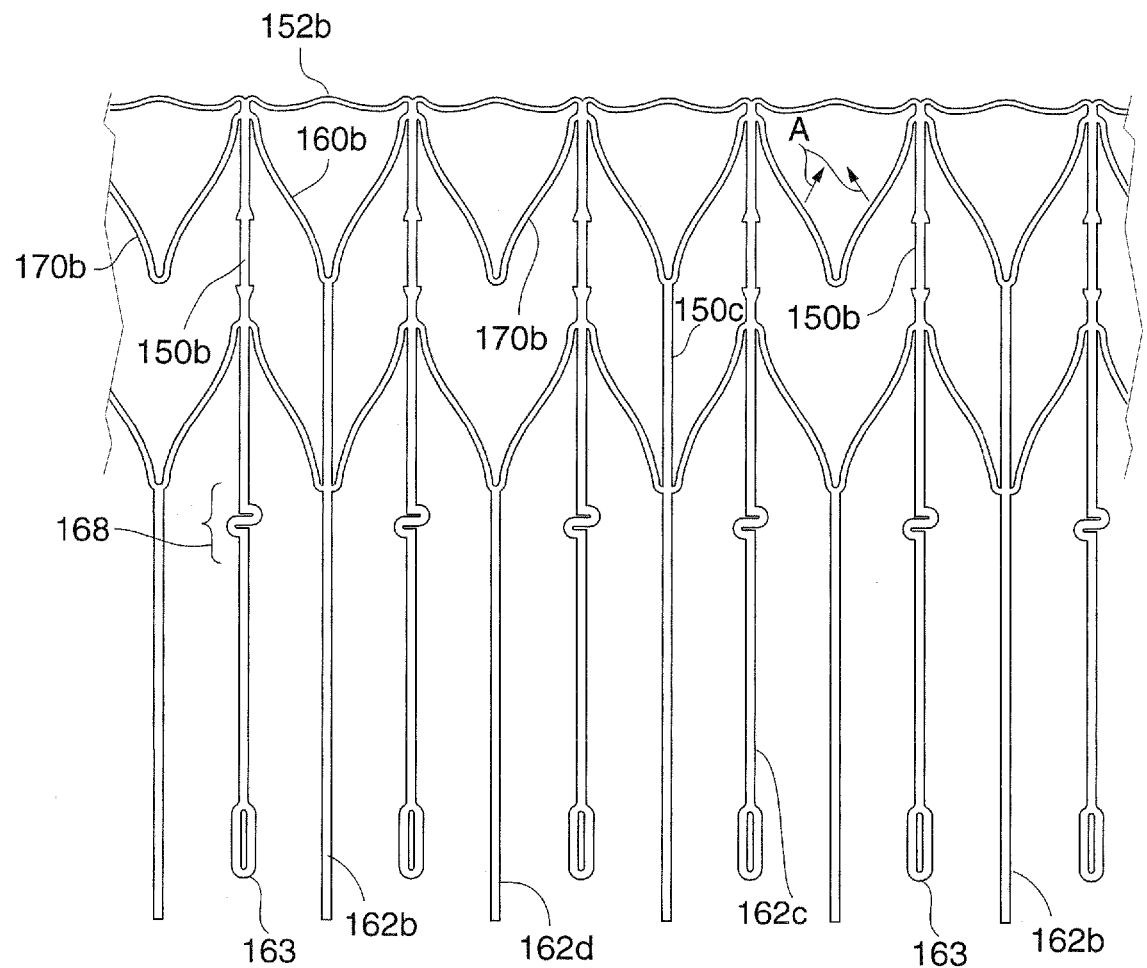
FIG. 8B is a plan view similar to the view of FIG. 5 showing the thromboembolic receiver of FIG. 8A.

Structural support members 160b are arranged in a distal row 171a adjacent to the cuff 152b, and a more proximal row 171b as shown in FIG. 8B. As with the FIG. 4 embodiment, a plurality of the structural support members 160b in the distal row are inwardly biased into the central lumen 147b of the receiver 146b so as to function as engagement members 170b for engaging a thromboembolism.

Three types of stabilizing strut members extend towards the proximal end of the receiver 146b. First, strut members 162b extend distally from the apexes of those of the structural support members 160b in the distal row 171a that do not function as engagement members. These strut members 162b are coupled at an intermediate point to the apexes of longitudinally aligned support members 160b in the proximal row 171b. Second, strut members 162c form the proximal extensions of the longitudinal strut members 150b and include eyelets 163 at their proximal ends. Third, strut members 162d extend from the apexes of those of the structure support members 160b in the proximal row that are longitudinally aligned with the engagement members 170b. Flexibility may be added to the receiver 146b may constructing some or all of the strut members to include flex regions of the type described in connection with earlier embodiments (see, e.g. flex regions 168 of FIG. 5).

Figure 8C:
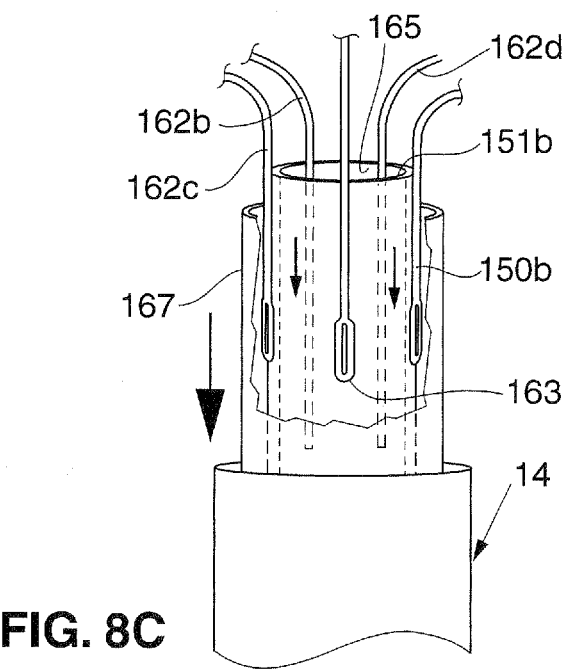
FIG. 8C is a perspective view of a proximal portion of the thromboembolic receiver of FIG. 8A and the distal portion of the elongate member coupled to the thromboembolic receiver, illustrating retraction of the thromboembolic receiver into a delivery and aspiration catheter.

Referring to FIG. 8C, the receiver 146b includes a pusher or elongate member 151b that includes a lumen 165 at its distal end. During assembly of the receiver 146b, the proximal ends of strut members 162b and 162d are positioned within the lumen 165 as shown and are allowed to slide freely within the lumen 165. The proximal ends of strut members 162c are bonded to the exterior surface of the elongate member 151b using heat shrink tubing 167 or other suitable material. The eyelets 163 facilitate bonding by allowing the bonding material to flow into the openings of the eyelets, thereby exposing a larger portion of each strut member 162c to the bonding material. If desired, the strut members 162b and 162d may be somewhat longer than the strut members 162c at the proximal end of the receiver, to allow them to be easily identified for insertion into the lumen 165 during assembly.

If it should be necessary to withdraw the receiver 146b back into the delivery and aspiration catheter 14 from a fully or partially deployed state, the elongate member 151b is withdrawn in a proximal direction relative to the catheter as shown in FIG. 8C. As the receiver 146b moves into the catheter 14, the receiver begins to fold at the apexes of the structural support members 160b, thereby pushing the strut members 162b and 162d in a proximal direction. Folding is more easily accomplished than with the receiver 146 of FIG. 4 due to the fact that certain of the structural support members 160b are interconnected at their apexes by strut members 162b. Thus, the folding of one member 160b in the proximal row 171b will facilitate the folding of a corresponding member 160b in the distal row 171a. The strut members 162b and 162d are allowed to slide freely within the lumen 165 of the elongate member 151b so that they will not resist folding of the members 160b during withdrawal of the receiver 146b into the catheter 14.

A first embodiment of a thromboembolic separator is shown in FIG. 9. The thromboembolic separator 16 of the first embodiment includes an elongated element 56 having a proximal end 58 and a distal end 60. The elongated element 56 may be constructed from any number of compositions having suitable biocompatibility and strength characteristics, and may be dimensioned in any number of suitable sizes and lengths depending upon the entry point into the vasculature, the location of the thromboembolism, variances in patient anatomy, and any extenuating circumstances. In an exemplary embodiment, the elongated element 56 may be constructed from stainless steel and/or Nitinol and dimensioned having a length ranging from 150 cm to 200 cm and a diameter ranging from 0.010 inch to 0.021 inch. A lubricious surface (e.g. a PTFE coating, hydrophilic coating, or other suitable coatings) may be applied to all or a portion of the elongate element 56 to facilitate movement of the element within the lumen of the delivery/aspiration catheter 14 and/or within the vasculature.

If desired, the elongate element 56 may take the form of a guide wire of the type used in various vascular applications. The elongate element may thus optionally include a coiled distal section 57 (FIG. 11B) having sufficient flexibility to prevent trauma to vascular tissues during advancement of the guidewire. In an exemplary embodiment, coiled distal section 57 may have a length in the range of approximately 27-33 cm.

The coil is preferably positioned around an inner mandrel or core (not shown) of a type commonly found in coiled guidewires.

The "working end" of the separator 16 includes a generally blunt tip element 62 attached or forming part of the distal end 60 of the elongated element 56, and a separator element 64 attached or forming part of the elongated element 56. The tip element 62 is preferably dimensioned to pass through or against a thromboembolism so as to soften or fragment the thromboembolism for removal. The blunt nature of the tip element 62 is advantageously atraumatic such that it will not cause damage to the interior of the vasculature during use. The separator 16 also assists in removing any clogs or flow restrictions that may develop within the lumen 36 due to the passage of thromboembolic material therethrough during aspiration.

In one embodiment, as best shown in FIG. 11A, the separator element 64 may take the form of a basket that is generally conical in shape, with an opening 66 facing proximally along the elongated element 56. The separator basket 64 is dimensioned to assist in the thromboembolic fragmentation process, as well as to receive such thromboembolic fragments to aid in their removal. In one embodiment, the separator basket 64 is provided having a web 68 and one or more support members 70. The support members 70 are dimensioned to bias the web 68 into the generally open position shown and, if desired, to allow the web 68 to assume a generally closed position (not shown, but generally flush against the elongated element 56) as the separator 16 is passed through delivery and aspiration catheter 14, a catheter-style pusher as described above, and/or the thromboembolism itself.

An alternative embodiment of a separator 16a is shown in FIGS. 11B and 11C, in which like reference numerals are used to identify features similar to those shown in FIGS. 9, 10 and 11A. Separator 16a differs from separator 16 of FIGS. 9, 10 and 11A primarily in the features of separator element 64a. Referring to FIG. 11B, separator element 64a is a conical member formed of a polymeric material such as polyurethane or Pebax® polyether block amides, to name a few. The separator element 64a is preferably a solid member, with a surface 65 facing in the proximal direction, and with the taper of the element oriented in a distal direction. Surface 65 may be contoured in a variety of ways. For example, surface 65 may be slightly concave as shown in FIG. 11B, substantially planar as shown in FIG. 11C, or slightly convex as shown in FIG. 11D.

The separator element 64a is positioned on the coiled distal section 57 of the elongate element 56. The pitch of a portion of the coiled section 57 may be decreased in certain regions of the coiled distal section 57. Opening the spacing in the coil in this manner can facilitate adhesion between the polymeric material of the separator element and the coil material during the molding process. The spacing between the separator element 64a and the distal end 60 of the elongate element 56 is preferably long enough to allow the distal-most portion of the elongate element sufficient flexibility to move atraumatically through the vasculature, but short enough to prevent folding of the distal-most portion during advancement of the elongate element 56. In an exemplary embodiment, the distal end of separator element 64a may be positioned approximately 3-9 mm from the distal end 60. It should be noted that the mandrel or core (not shown) within the coiled section 57 of the elongate element 56 might have a tapered diameter selected to enhance the flexibility of the coiled section.

A handle member 72 (FIG. 9) is provided at the proximal end 58 of the separator to provide a purchase point for a user to advance and/or manipulate the atraumatic tip element 62 and separator 64/64a. In one embodiment, the handle member 72 may be coupled to the elongated element 56 in any suitable fashion, including but not limited to providing a generally rigid extension (not shown) disposed within the elongated element 56 for the purpose of coupling the two components together. This coupling may be augmented or strengthened through the use of any number of adhesives or fusing techniques.

The separator 16 may be provided in a variety of different permutations without departing from the scope of the present invention. For example, in addition to the "self deployable" embodiment described above, the separator basket 64 of FIG. 11A may be selectively deployed, such as by equipping the separator basket 64 with a mechanism to selectively bias or open the support members 70 from an initial position lying generally flush against the elongated element 56 to a generally radially expanded position (shown with arrows in FIG. 11A).

It will be appreciated that the guide and occlusion catheter 12, the delivery and aspiration catheter 14, the thromboembolic separator 16 and/or the thromboembolic receiver 46 may be provided with any number of features to facilitate the visualization of these elements during introduction and usage, including but not limited to having the distal regions equipped with radiopaque markers for improved radiographic imaging.

As discussed previously in connection with FIG. 1, the various components described herein may be provided as part of a system 10 for removing thromboembolic material. The thromboembolic removal system 10 may include a guide and occlusion catheter 12, a delivery and aspiration catheter 14, a thromboembolic separator 16/16a, a thromboembolic receiver (e.g. receiver 46 or 146), and an aspiration pump 18, as well as guidewires and/or other tools appropriate for the procedure. In one embodiment, multiple receivers 46/146 may be provided, allowing the surgeon to sequentially retrieve several thromboembolisms during the course of a procedure. For simplicity, each separate receiver may be provided with a separate delivery and aspiration catheter. The system 10 may additionally be provided with instructions for use setting forth any of the various methods of use described herein, or equivalents thereof.

System Use

Figure 12:
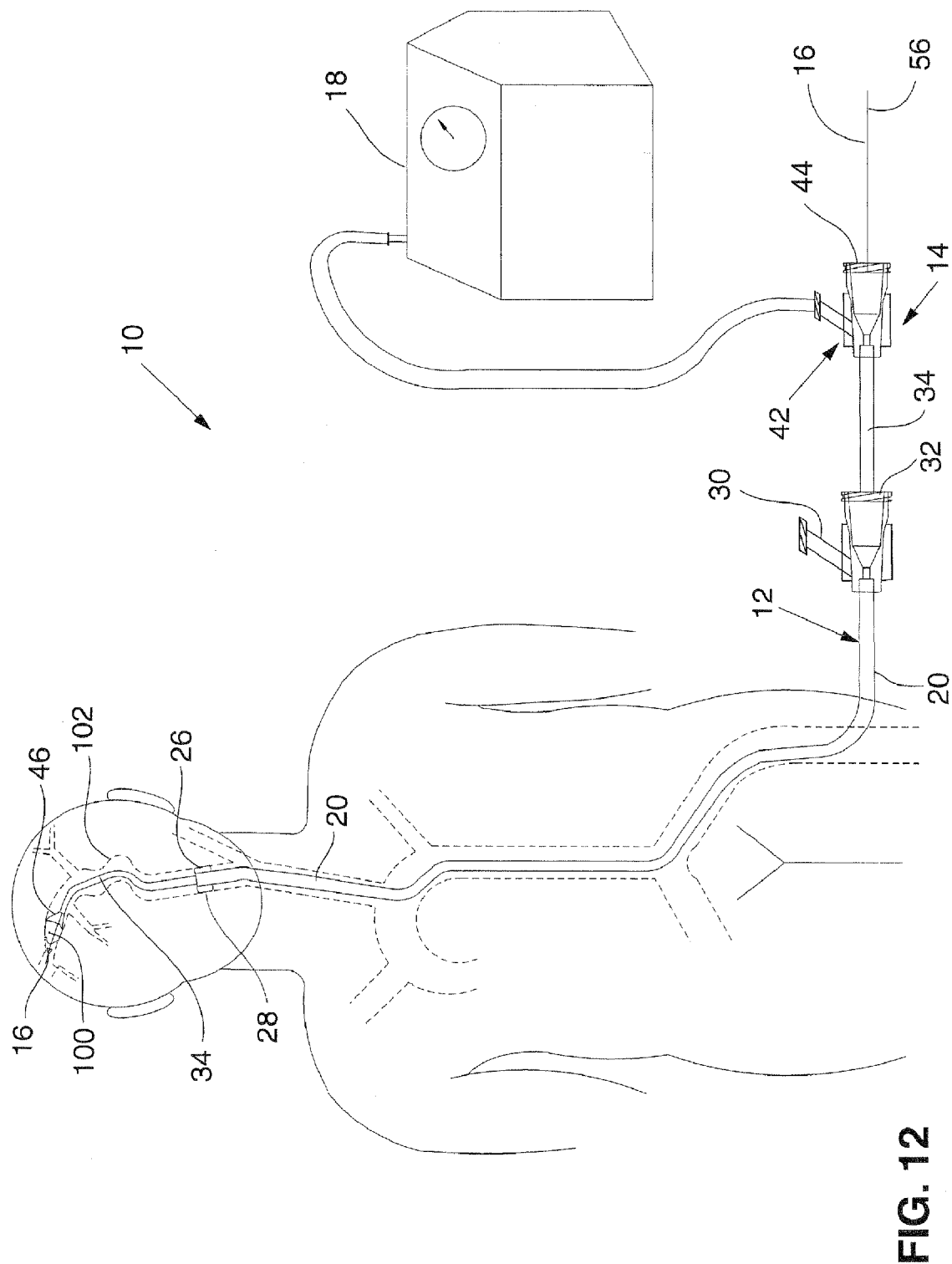
FIG. 12 is a partial sectional view of a patient illustrating the thromboembolic removal system of FIG. 1 in use within the arterial system.
Figure 13:
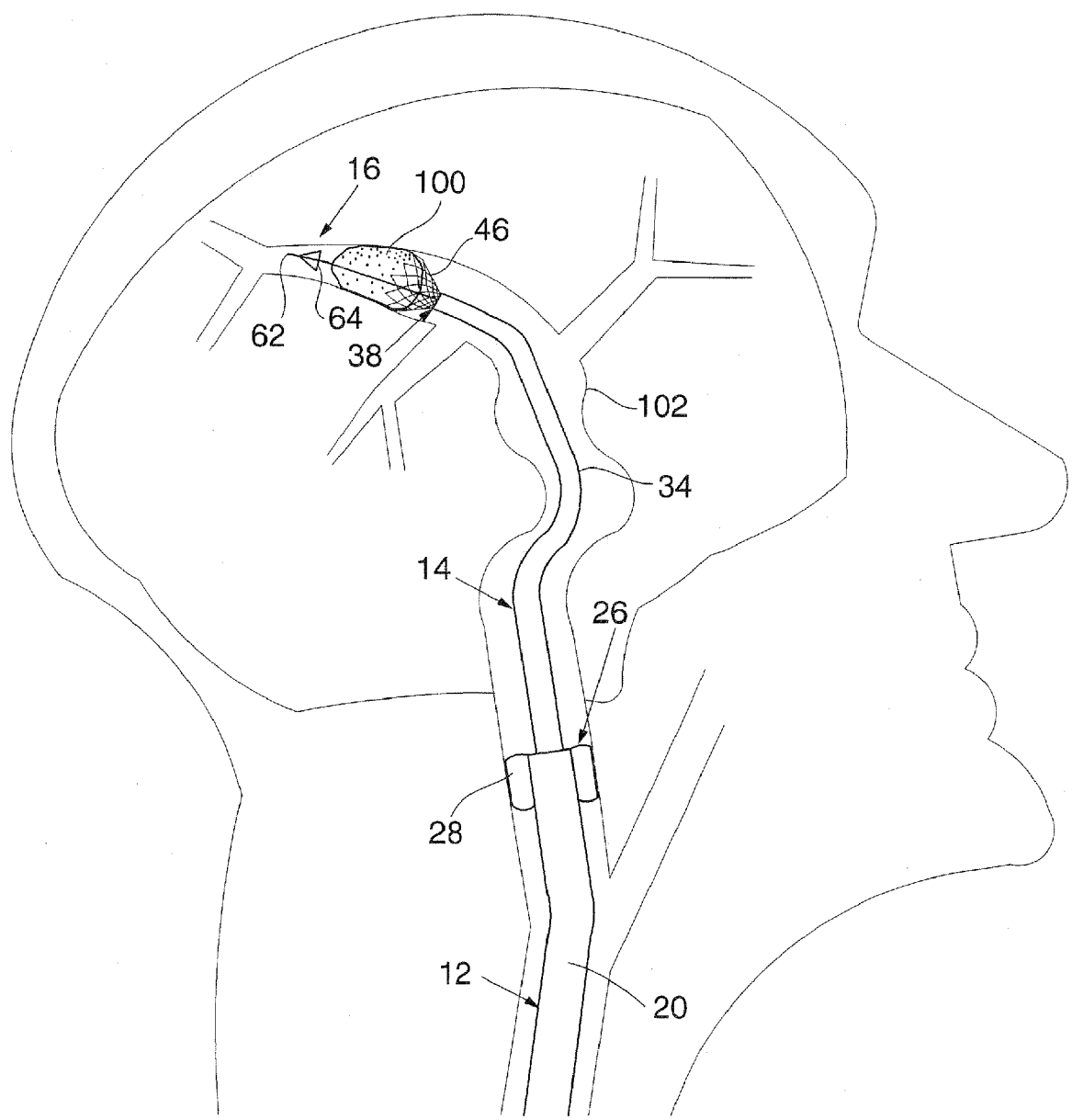
FIG. 13 is a partial sectional view of a patient illustrating the distal region of the thromboembolic removal system of FIG. 1 in use within a cerebral artery.

Methods of using the thromboembolic removal system 10 will now be described with reference to FIGS. 12-28. As shown generally in FIGS. 12-13, in a first exemplary method the thromboembolic removal system 10 is introduced into the patient's vasculature, such as via the Seldinger technique. FIG. 14 illustrates the first step of this process, which involves advancing a guide wire 104 to a point proximal to a thromboembolism 100. The guide wire 104 may comprise any number of commercially available guide wires, the operation of which is well known in the art. However, in one method, the elongate member 56 (FIG. 11B) of the separator 16 functions as the guidewire 104.

FIG. 15 illustrates a second step, which involves advancing the guide and occlusion catheter 12 over the guide wire 104 to a point proximal to the thromboembolism. The next step, shown in FIG. 16, preferably involves inflating the balloon occlusion member 28 so as to arrest the blood flow within the cerebral artery 102 containing the thromboembolism 100. As shown in FIG. 17, the delivery and aspiration catheter 14 is then advanced through the guide and occlusion catheter 12 such that the distal end 38 of the delivery and aspiration catheter 14 is positioned at a point proximal to the thromboembolism 100. This may be facilitated by advancing the delivery and aspiration catheter 14 over the guide wire 104 and/or an exchange-length guide wire (not shown but well known in the art) extending through the guide and occlusion catheter 12.

At this point, as shown in FIG. 18, the thromboembolic receiver 46 is deployed from the distal end 38 of the delivery and aspiration catheter 14. In one embodiment, the balloon occlusion 28 may be inflated at this point (as opposed to inflating it before the delivery and aspiration catheter 14 is advanced, as shown in FIG. 16). The delivery and aspiration catheter 14 is then advanced distally—as shown in FIG. 19—such that the thromboembolic receiver 46 engages and/or envelops (partially or fully) the thromboembolism 100. At this point, as shown in FIGS. 20 and 21, the delivery and aspiration catheter 14 may be withdrawn into the guide and occlusion catheter 12 to remove the thromboembolism 12 from the patient 16.

To augment the ability to remove the thromboembolism 100, or in the instance the thromboembolic receiver 46 does not initially engage the thromboembolism 100, the aspiration pump 18 may be activated to establish negative pressure within the delivery and aspiration catheter 14. In this fashion, negative pressure will be created within the cerebral artery 102 and exerted upon the thromboembolism 100. As noted above, the separator 16 (or the separator 16a of FIGS. 11B-D) may be employed during this process (e.g. advancing and retracting it within the lumen 36 of the delivery and aspiration catheter 14) to remove any clogs or flow restrictions due to the passage of thromboembolic material through the lumen 36. The negative pressure will serve to draw the thromboembolism 100 into (partially or fully) the thromboembolic receiver 46. The delivery and aspiration catheter 14 may then be withdrawn into the guide and occlusion catheter 12 to remove the thromboembolism 100 from the patient.

Figure 22:
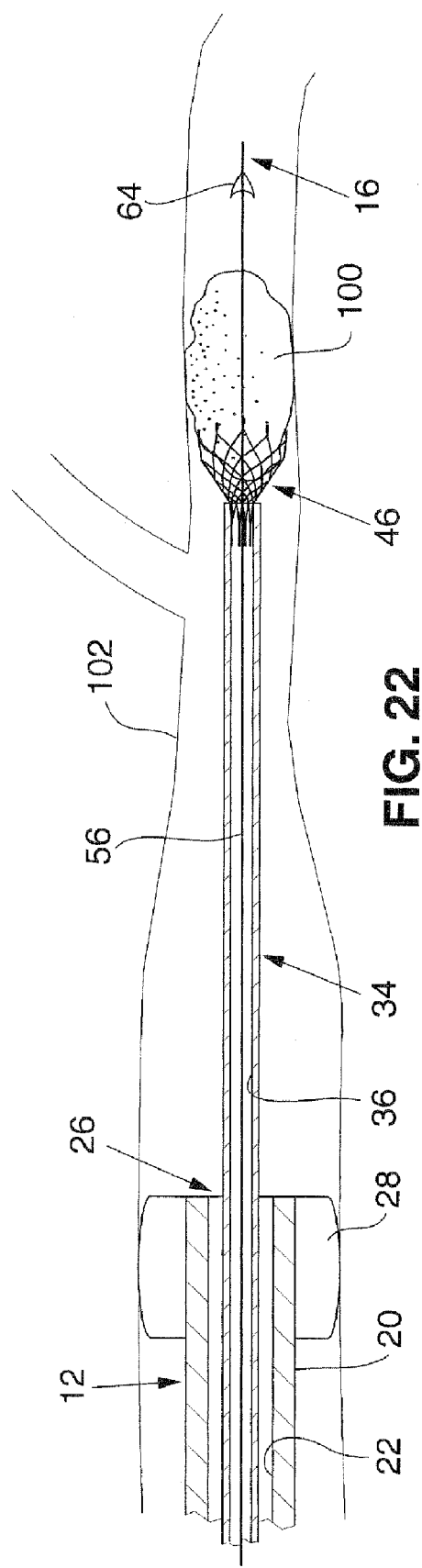
FIG. 22 is a partial section side view illustrating use of the thromboembolic separator of FIGS. 1 and 9-11C to engage the distal end of the thromboembolism.

To further augment the ability to remove the thromboembolism 100, or in the instance the aspiration pump 18 does not adequately draw all or most of the thromboembolism 100 into the receiver 46, the thromboembolic separator 16/16a may be advanced into contact with a portion of the thromboembolism, or completely through the thromboembolism 100 as shown in FIG. 22, and employed to bias or engage the distal end of the thromboembolism 100. This will increase the surface area of engagement with the thromboembolism 100, which will advantageously allow it to be withdrawn into the guide and occlusion catheter 12 such as by withdrawing the separator 16/16a and delivery and aspiration catheter 14 simultaneously into the guide and occlusion catheter 12.

Figure 23:
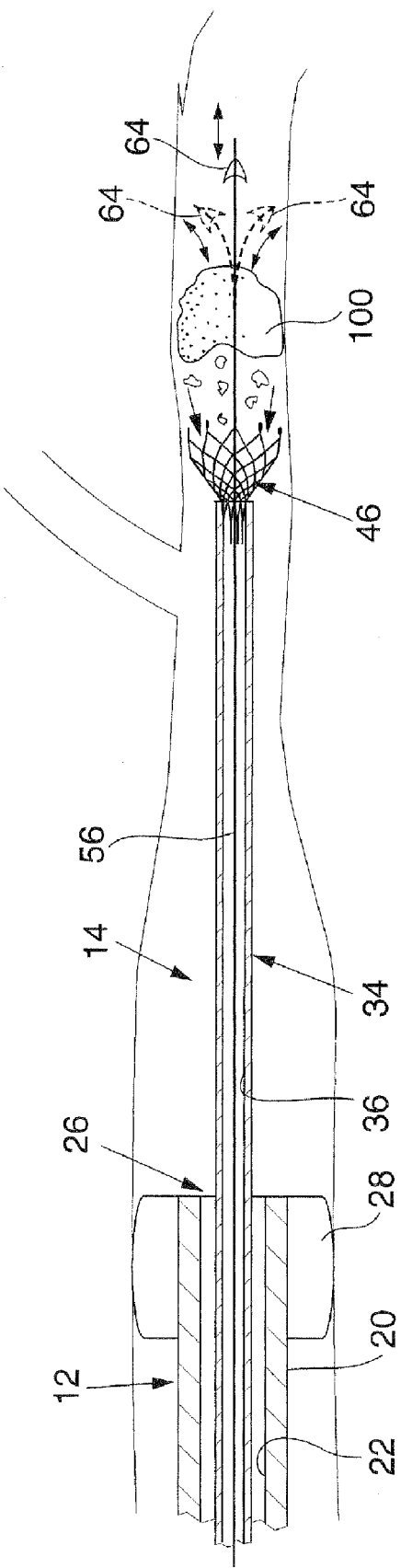
FIG. 23 is a partial section side view illustrating use of the thromboembolic separator of FIGS. 1 and 9-11C to fragmentize and/or soften the thromboembolism and/or aid aspiration.

As shown in FIG. 23, the separator 16/16a may also be selectively advanced and retracted through the thromboembolism 100 (or that remaining outside the receiver 46). This will serve to break up or otherwise soften the thromboembolism 100. Advancing and retracting the separator 16/16a also serves to remove any clogs or flow restrictions within the lumen of the delivery and aspiration catheter 14 during aspiration due to the passage of thromboembolic material through the lumen 36 of the delivery and aspiration catheter 14. In either event, the aspiration pump 18 will draw or bias the thromboembolic fragments 106 or the softened thromboembolism 100 into the thromboembolic receiver 46 and/or into catheter 14. The delivery and aspiration catheter 14 may then be withdrawn such that the thromboembolic receiver 46 is drawn into the guide and occlusion catheter 12 to remove the thromboembolism 100 from the patient.

Selective advancement of the separator element 64 through the thromboembolism and retraction of the separator element into the delivery and aspiration catheter 14, preferably in combination with aspiration, can additionally be used to carry small "bites" of the thromboembolic material into the catheter 14. For example, the separator element 64 may be passed through the thromboembolic material, displacing some material and thus forming a channel in the material as it moves distally. Once the separator element is positioned further into, or distally of, the thromboembolism, some of the displaced material may flow back into this channel. Subsequent retraction of the separator element 64 through the material (e.g. through the re-filled channel) will then draw some of the material into the catheter 14. To facilitate this procedure, the separator element 64 and the catheter 14 are preferably provided with fairly tight tolerances between the diameter of the catheter lumen 36 and the greatest diameter of the separator element 64. For example, in one exemplary embodiment, the outer diameter of separator element 64 and the diameter of lumen 36 may differ by approximately 0.003-0.008 inches.

An alternative method will next be described in which the receiver and disrupter are preferably used independently of one another, although combined use such as that described in connection with the first exemplary method might also be used. This method will be described as performed using the thromboembolic receiver 146 and the separator 16a, however it should be appreciated that other embodiments of these components may alternatively be used in the disclosed method.

According to the alternative method, an initial determination is made concerning whether use of receiver 146 or separator 16a will first be employed. This determination may be made at random, although in a preferred method the surgeon selects the appropriate tool based on a determination of the likely nature of the thromboembolic material that is to be removed. In particular, the surgeon will assess the patient to determine whether the material is likely to be hard or soft/gelatinous. This assessment might include an evaluation of one or more factors such as the response of the tip of the guidewire or separator when it is brought in contact with the thromboembolism, the location of the thromboembolic material, patient symptoms, and/or the manner in which the stroke caused by the thromboembolism is manifesting itself.

As discussed in connection with the first exemplary method, the guide and occlusion catheter 12 is introduced into the patient's vasculature, and the occlusion balloon 28 is inflated to arrest the flow of blood within the vessel (see, for example, FIGS. 14-16).

The delivery and aspiration catheter 14 is passed through the guide and occlusion catheter 12 and positioned with its distal end at a location proximal to the thromboembolism 100. If the surgeon elects to use the separator 16a prior to using the receiver 146, or if the assessment results in a determination that the thromboembolic material is likely to be somewhat soft or gelatinous, the aspiration pump 18 is activated to establish negative pressure within the delivery and aspiration catheter 14, and thus to exert negative pressure exerted upon the thromboembolism 100 to draw embolic material into the catheter 14.

The separator 16a is deployed from the distal end of the delivery and aspiration catheter 14 and moved into contact with the thromboembolic material 100 as shown in FIG. 24. The separator may be advanced and retracted multiple times if desired. When advanced and retracted as shown, the separator can facilitate aspiration of the thromboembolic material into the catheter 14 in one of a variety of ways. First, movement of the separator into contact with the thromboembolism can loosen, separate, or soften pieces of thromboembolic material, such that pieces of the thromboembolism can be aspirated into the catheter. Second, advancing and retracting the separator 16a serves to remove any clogs or flow restrictions within the lumen 36 of the delivery and aspiration catheter 14 that might be caused by the passage of thromboembolic material through the lumen 36. Additionally, during retraction of the disrupter 16a, its proximal surface 35 may push or plunge loosened material towards and/or into the distal end of the catheter 14 for subsequent aspiration out of the body.

If use of the disrupter 16a as just described reveals that the vessel includes a hard mass of thromboembolic material incapable of aspiration without further intervention, the disrupter 16a is preferably withdrawn from the catheter 14 and a thromboembolic receiver 146 is passed through the delivery and aspiration catheter 14 and deployed within the blood vessel. If the system is provided with multiple sizes of receivers, the surgeon will select a receiver having an appropriate size for the blood vessel being treated.

Referring to FIGS. 25-28, once the receiver 146 is deployed, it expands into contact with the surrounding walls of the vessel. As the receiver 146 is advanced towards the body thromboembolic material 200, the walls of the receiver 146 slip around the body 200 to engage and/or envelop (partially or fully) the thromboembolism. The engaging elements 170 engage the thromboembolism 200, thereby retaining it within the receiver. If desired, the delivery and aspiration catheter 14 may be advanced slightly in a distal direction as indicated by arrows in FIG. 27, so as to "cinch" the strut members 162 towards one another, thus causing the receiver 146 to collapse slightly in a radially inward direction. Additionally, the aspiration pump 18 (FIG. 1) may be activated to facilitate retention of the thromboembolism 200 within the receiver. The delivery and aspiration catheter 14, the receiver 146 and the thromboembolism 100 are withdrawn into the guide and occlusion catheter 12 and are withdrawn from the body. If additional thromboembolic material should remain in the blood vessel, a new delivery and aspiration catheter 14 may be passed into the blood vessel, and a new receiver may be deployed through the catheter 14 for retrieving the additional body of thromboembolic material.

Naturally, the surgeon may elect to initially deploy the receiver rather than the separator, such as if the initial assessment results in a determination that the thromboembolic material is likely to be hard. The method is then carried out utilizing the receiver 146 as described in the preceding paragraph. If it is later determined that residual thromboembolic material (e.g. soft or gelatinous material) is present in the vessel, the receiver 146 is preferably removed from the body, and the separator 16a is passed through the delivery and aspiration catheter 14. The aspiration pump 18 is activated and the separator 16a is manipulated to facilitate aspiration of the soft material in the manner described above.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention.

We claim:

1. An apparatus for withdrawing thromboembolic material from a blood vessel, the apparatus comprising:
   an elongate member; and
   a receiver on a distal portion of the elongate member, the receiver formed of a plurality of structural members arranged to form a sleeve having a central lumen, a first plurality of the structural members comprising longitudinally extending struts, a second plurality of the structural members comprising v-shaped engaging elements, and a third set of structural members comprising a plurality of axially spaced-apart circumferential rings attached to the longitudinal struts, each of said v-shaped engaging elements being disposed between adjacent ones of the longitudinal struts and including a first leg extending into the central lumen from a first longitudinal strut and a second leg extending into the central lumen from a second, adjacent longitudinal strut, said first and second legs attached to one another within the central lumen to define a plurality of longitudinally oriented apexes extending into the central lumen, wherein at least a distal row and a proximal row of the v-shaped engaging elements are disposed between a distal circumferential ring and a proximal circumferential ring and each apex is unattached to any other structure within the central lumen.

2. The apparatus of claim 1, wherein the receiver is radially expandable from a compressed position in which the receiver is sized for passage into a blood vessel, to an expanded position in which the receiver is sized to contact an inner surface of the blood vessel when at body temperature.

3. The apparatus of claim 2, wherein, in the expanded position, the receiver is slidable over a body of thromboembolic material within the blood vessel to receive the body into the central lumen, and wherein the engaging elements are oriented to engage the body within the lumen.

4. The apparatus of claim 2, wherein, in the expanded position, the receiver has a maximum expanded diameter in the range of approximately 2-6 mm.

5. The apparatus of claim 2, wherein, in the expanded position, the receiver has a maximum expanded diameter in the range of approximately 6-9 mm.

6. The apparatus of claim 2, further including a catheter having a catheter lumen, the receiver insertable into the catheter lumen when in the compressed position, the receiver configured such that advancement of the receiver out of the catheter causes the receiver to self-expand to its expanded position.

7. The apparatus of claim 6, wherein the receiver is configured such that withdrawal of the receiver into the catheter causes the receiver to collapse to the compressed position.

8. The apparatus of claim 1, wherein the distal circumferential ring is positioned at a distal end of the receiver.

9. The apparatus of claim 1, wherein the proximal circumferential ring is positioned at a proximal end of the receiver.

10. The apparatus of claim 1, wherein a plurality of the longitudinal struts extend between the circumferential rings.

11. The apparatus of claim 1, wherein each longitudinal strut includes at least one spring region.

12. The apparatus of claim 1, wherein the plurality of circumferential rings includes an intermediate ring, and wherein the distal row of v-shaped elements is positioned between the distal ring and the intermediate ring, and the proximal row of v-shaped elements is positioned between the intermediate ring and the proximal ring.

13. The apparatus of claim 1, further including:
an elongate sheath having a sheath lumen proportioned to receive the elongate member; and
an occlusion balloon on the sheath, the balloon inflatable to occlude flow of blood within a blood vessel.

14. The apparatus of claim 1, wherein the receiver is expandable from a first position to a second, radially expanded position, and wherein the engaging elements are foldable during movement of the receiver from the second position to the first position.

15. The apparatus of claim 1, further comprising a plurality of v-shaped elements which include apex regions peripheral to the central lumen.

16. An apparatus for withdrawing thromboembolic material from a blood vessel, the apparatus comprising:
an elongate member; and
a receiver on a distal portion of the elongate member, the receiver formed of a plurality of structural members arranged to form a sleeve having a central lumen, the structural members including longitudinal strut members, v-shaped engaging elements and a plurality of axially spaced-apart circumferential rings attached to the longitudinal struts, each v-shaped engaging element being disposed between adjacent ones of the longitudinal struts and including a first leg extending from a first longitudinal strut member and a second leg extending from a second longitudinal strut member from a fixed position thereon, said second longitudinal strut member adjacent to the first longitudinal strut member, the first leg forming an apex with the second leg, the apex extending into the central lumen, wherein at least a distal row and a proximal row of the v-shaped engaging elements are disposed between a distal circumferential ring and a proximal circumferential ring and wherein the first and second legs extend from a position that is longitudinally fixed relative to the first and second strut members and each apex is unattached to any other structure within the central lumen.

17. The apparatus according to claim 16, wherein the longitudinal strut members have distal ends and the distal circumferential ring extends between the distal ends of the longitudinal strut members, the distal circumferential ring formed of a plurality of strut members extending generally perpendicular to the longitudinal strut members.

18. The apparatus of claim 17, wherein the receiver has a distal end, wherein the longitudinal strut members extend to the distal end of the receiver, and the distal circumferential ring is on the distal end of the receiver.

19. The apparatus of claim 18, wherein the receiver has a proximal end, and wherein the longitudinal strut members extend between the distal and proximal ends of the receiver.

20. The apparatus of claim 17, wherein the elongate member is a tubular member, wherein the longitudinal strut members include proximal ends coupled to the tubular member.

21. The apparatus of claim 17 wherein: the receiver is radially expandable from a compressed position to an expanded position and the plurality of circumferential rings include a plurality of bend regions, the circumferential rings bendable at the bend regions during movement of the receiver from the expanded position to the compressed position.

22. The apparatus of claim 16, wherein the receiver is expandable from a first position to a second, radially expanded position, and wherein the engaging elements are foldable during movement of the receiver from the second position to the first position.

23. The apparatus of claim 16, wherein the distal circumferential ring defines an opening to the central lumen.

* * * * *